(12) United States Patent
Mahajan

(10) Patent No.: US 7,060,480 B2
(45) Date of Patent: Jun. 13, 2006

(54) MRE11 ORTHOLOGUE AND USES THEREOF

(75) Inventor: Pramod B. Mahajan, Urbandale, IA (US)

(73) Assignee: Pioneer Hi-Bred International, Inc., Johnston, IA (US)

(*) Notice: Subject to any disclaimer, the term of this patent is extended or adjusted under 35 U.S.C. 154(b) by 0 days.

(21) Appl. No.: 10/650,108

(22) Filed: Aug. 26, 2003

(65) Prior Publication Data
US 2004/0068768 A1    Apr. 8, 2004

Related U.S. Application Data

(62) Division of application No. 09/835,654, filed on Apr. 16, 2001, now Pat. No. 6,646,182.

(60) Provisional application No. 60/198,570, filed on Apr. 19, 2000.

(51) Int. Cl.
*C12N 9/16* (2006.01)
*C12N 1/20* (2006.01)
*C12N 15/00* (2006.01)
*C12P 21/04* (2006.01)
*C07H 21/04* (2006.01)

(52) U.S. Cl. .................... 435/196; 435/440; 435/252.3; 435/320.1; 435/69.1; 435/71.1; 536/23.2; 536/23.6

(58) Field of Classification Search ................ 435/196, 435/440, 320.1, 252.3, 69.1, 71.1; 536/23.2, 536/23.6
See application file for complete search history.

(56) References Cited

U.S. PATENT DOCUMENTS 5,500,365 A    3/1996    Fischhoff et al.

FOREIGN PATENT DOCUMENTS

| WO | WO 97/08331 A1 | 3/1997 |
|---|---|---|
| WO | WO 99/37789 A1 | 7/1999 |
| WO | WO 99/41394 A1 | 8/1999 |
| WO | WO 00/12716 A2 | 3/2000 |
| WO | WO 00/15816 A3 | 3/2000 |
| WO | WO 00/42205 A2 | 7/2000 |

OTHER PUBLICATIONS

Sequence Alignment—Seq Id No.:2 and T52564.*
Chamankhah et al., Isolation of hMRE11B: failure to complement yeast mre11 defects due to species-specific protein interactions, Gene 225:107-116 (1998).
Tavassoli et al., Cloning and characterisation of the *Schizosaccharomyces pombe* rad32 gene: a gen required for repair of double strand breaks and recombination, Nucleic Acids Res. 23(3):383-388 (1995).
Usui et al., Complex Formation and Functional Versatility of Mre11 Budding Yeast in Recombination, Cell 95:705-716 (1998).
Lee et al., *Saccharomyces* Ku70, Mre11/Rad50 and RPA Proteins Regulate Adaptation to G2/M Arrest after DNA Damage, Cell 94:399-409 (1998).
Carney et al., The hMre11/hRad50 Protein Complex and Nijmegen Breakage Syndrome: Linkage of Double-Strand Break Repair to the Cellular DNA Damage Response: Cell 93:477-486 (1998).
Tsukamoto et al., Effects of Mutations of RAD50, RAD51, RAD52, and Related Genes on Illegitimate Recombination in *Saccharomyces cerevisiae*, Genetics 142:383-391 (1996).
Paull et al., The 3' to 5' Exonuclease Activity of Mre11 Facilities Repair of DNA Double-Strand Breaks, Molecular Cell 1:969-979 (1998).
Trujillo et al., Nuclease Activities in a Complex of Human Recombination and DNA Repair Factors Rad50, Mre11, and p95, J. Biol. Chem. 273(34):21447-21450 (1998).
Ajimura et al., Identification of New Genes Required for Meiotic Recombination in *Saccharomyces cerevisiae*, Genetics 133:t51-66 (1993).
Johzuka et al., Interaction of Mre11 and Rad50: Two Proteins Required for DNA Repair and Meiosis-Specific Double-Strand Break Formation in *Saccharomyces cerevisiae*, Genetics 139:1521-1532 (1995).
Petrini et al., Isolation and Characterization of the Human MRE11 Homologue, Genomics 29:80-86 (1995).
Furuse et al., District roles of two seperable in vitro activities of yease Mre11 in mitotic and meiotic recombination, EMBO Journal 17(21):6412-6425 (1998).
Xiao et al., Conditional gene targeted deletion by Cre recombinase demonstrates the requirement for the double-strand break repair Mre11 protein in murine embryonic stem cells, Nucleic Acids Res. 25(15):2985-2991 (1997).
Yamaguchi-Iwai et al., Mre11 is essential for the maintenance of chromosomal DNA in vertebrate cells, EMBO Journal 18(23):6619-6629 (1999).
Wilson et al., the role of *Schizosaccharomyces pombe* Rad32, the Mre11 homologue, and other DNA damage response proteins in non-homologous end joining and telomere length maintenance, Nucleic Acids Res. 27(13):2655-2661 (1999).

(Continued)

*Primary Examiner*—Ponnathapu Achutamurthy
*Assistant Examiner*—Yong D. Pak
(74) *Attorney, Agent, or Firm*—Pioneer Hi-Bred International, Inc.

(57) ABSTRACT

The invention provides isolated Mre11 nucleic acids and their encoded proteins. The present invention provides methods and compositions relating to altering Mre11 levels in plants. The invention further provides recombinant expression cassettes, host cells, transgenic plants, and antibody compositions.

2 Claims, No Drawings

OTHER PUBLICATIONS

Dolganov et al., Human Rad50 is Physically Associated with Human Mre11:Identification of a conserved Multiprotein Complex Implicated in Recombinational DNA Repair, Mol. Cell. Biol. 16(9):4832-4841 (1996).

Lewis et al., Repair of Endonuclease-Induced Double-Strand Breaks in *Saccharomyces cerevisiae*: Essential Role for Genes Associated with Nonhomologous End-Joining, Genetics 152:1513-1539 (1999).

Moore et al., Cell Cycle and Genetic Requirements of Two Pathways of Nonhomologous End-Joining Repair of Double-Strand Breaks in *Saccharomyces cerevisiae*, Mol. Cell Biol. 16(5):2164-2173 (1996).

Nairz et al., mre11S-yeast mutation that blocks doublestand-break processing and permits nonhomologous synapsis in meiosis, Genes & Development 11:2272-2290 (1997).

Tsubouchi et al., A Novel mre11 Mutation Impairs Processing of Double-Strand Breaks of DNA during Both Mitosis and Meiosis, Mol. Cell. Biol. 18(1):260-268 (1998).

Hartung et al., Accession No. Q9XGM2, *Arabidopsis thaliana* (Mouse-ear cress), (1999).

Hartung et al., Accession No. AJ243822, *Arabidopsis thaliana* mRNA for Mre11 protein (MRE11 gene), (1999).

Gerecke et al., Accession No. AF178433, *Coprinus cinereus* DNA repair and Meiosis protein Mre11 (mre11) gene, complete cds (1999).

Bibikova et al., Accession No. AF134569, *Xenopus laevis* putative nuclease Mre11 (MRE11) mRNA, complete cds (1999).

Brodsky et al., Accession No. AF132144, *Drosophila melanogaster* clone LD8638 endo/exonuclease Mre11 (mre11) mRNA, complete cds (1999).

Hartung et al., Isolation of the Complete cDNA of the Mre11 Homologue of *Arabidopsis* (Accession No. AJ243822) Indicated Conservation of DNA Recombination Mechanisms Between Plants and Other Eucaryotes, Plant Gene Register PGR99-132 Plant Physiol. 121:132 (1999).

Nakamura, Y., EMBL Accession No. AB010695, *Arabidopsis thaliana* genomic DNA, chromosome 5, P1 clone:MDK 4 (1998).

Jaesung et al., Accession No. PREV199800510932, *Agrobacterium tumefaciens* transformation of the*thaliana* mutants uvh1 and rad5 (1998).

Nam et al., *Agrobacterium turnefaciens* Transformation of the Radiation Hypersensitive *Arabidopsis thaliana* Mutants uvh1 and rad5, MPMI 11(11):1136-1141 (1998).

Mysore et al., An arabidopsis histone H2A mutant is deficient in Agrobacterim T-DNA integration, PNAS 97(2):948-953 (2000).

Lewin, B., Most eukaryotic mRNAs are polyadenylated at the 3' end, Genes V 10:264-165 (1994), Oxford University Press, New York.

Doerks, T., Protein annotation: detective work for function prediction, TIG 14(6):248-250 (1998).

Smith et al., The challenges of genome sequence annotation or "The devil is in the details", Nature Biotechnology 15:1222-1223 (1997).

Brenner, S.E., Errors is genome annotation, TIG 15(4):132-133 (1999).

Bork et al., Go hunting in sequence databases but watch out for the traps, TIG 12(10):425-427 (1996).

Van De Loo et al., An oleate 12-hydroxylase from *Ricinus communis L*, is a fatty acyl desatruase homolog, Proc. Natl. Acad, Sci. USA 92:6743-6747 (1995).

\* cited by examiner

```
                         SEQUENCE LISTING

<160> NUMBER OF SEQ ID NOS: 9

<210> SEQ ID NO 1
<211> LENGTH: 2597
<212> TYPE: DNA
<213> ORGANISM: Zea mays
<220> FEATURE:
<221> NAME/KEY: CDS
<222> LOCATION: (151)...(1806)

<400> SEQUENCE: 1
gacccacgcg tccggccggc ccttctcttc ccttgctgct gtgcgaaccc gagcgcccaa      60
acctgaactt aagctatttg gggctacttg tatttggaaa aaatatatcg ggtcctttac     120
tggtccgccg gtgttatttt aacttatgaa atg gtt ggt ttt tgc agt gca tta     174
                                Met Val Gly Phe Cys Ser Ala Leu
                                 1               5 gat tta cag caa cgg att ggt ttg gcc aac acg ttg agt tca ggt tca     222
         Asp Leu Gln Gln Arg Ile Gly Leu Ala Asn Thr Leu Ser Ser Gly Ser
              10                  15                  20
```

-continued

```
atg tct gaa cca gca caa cct agt gga ggg gaa ggt gat gtc aac acg      270
Met Ser Glu Pro Ala Gln Pro Ser Gly Gly Gly Asp Val Asn Thr
 25                  30                  35                  40 ctc cga ata ctt gta gca acc gac tgc cat cta ggc tac atg gag aaa      318
Leu Arg Ile Leu Val Ala Thr Asp Cys His Leu Gly Tyr Met Glu Lys
                 45                  50                  55 gat gag ata cgt agg ttt gat tcc ttt caa gca ttt gag gag att tgc      366
Asp Glu Ile Arg Arg Phe Asp Ser Phe Gln Ala Phe Glu Glu Ile Cys
             60                  65                  70 gca ttg gca gat aaa aat aag gtg gat ttt ata ctt ctc ggt ggt gat      414
Ala Leu Ala Asp Lys Asn Lys Val Asp Phe Ile Leu Leu Gly Gly Asp
         75                  80                  85 cta ttc cat gag aac aag ccg tca cgc tca acc ctg gta aaa acg att      462
Leu Phe His Glu Asn Lys Pro Ser Arg Ser Thr Leu Val Lys Thr Ile
     90                  95                 100 gag att cta cgg cgc tac tgc cta aat gat caa cct gtg aag ttc cag      510
Glu Ile Leu Arg Arg Tyr Cys Leu Asn Asp Gln Pro Val Lys Phe Gln
105                 110                 115                 120 gtt gtc agt gat cag aca gtt aac ttt cca aac agg ttt ggt aag gta      558
Val Val Ser Asp Gln Thr Val Asn Phe Pro Asn Arg Phe Gly Lys Val
                125                 130                 135 aat tat gaa gac cca aac ttt aac gtt ggt ctg cct gtg ttc acc att      606
Asn Tyr Glu Asp Pro Asn Phe Asn Val Gly Leu Pro Val Phe Thr Ile
            140                 145                 150 cat gga aat cat gat gac cct gct gga gtg gat aat ctc tct gct atc      654
His Gly Asn His Asp Asp Pro Ala Gly Val Asp Asn Leu Ser Ala Ile
        155                 160                 165 gat att ctt tcg gct tgc aat ctt gta aat tat ttt gga aag atg gac      702
Asp Ile Leu Ser Ala Cys Asn Leu Val Asn Tyr Phe Gly Lys Met Asp
    170                 175                 180 ctt ggt ggc tct ggc gtt ggt cag ata gca gtt tat cct gta ctt gta      750
Leu Gly Gly Ser Gly Val Gly Gln Ile Ala Val Tyr Pro Val Leu Val
185                 190                 195                 200 aaa aag ggc atg act tca gtt gca ctg tat ggt ctt gga aac att aga      798
Lys Lys Gly Met Thr Ser Val Ala Leu Tyr Gly Leu Gly Asn Ile Arg
                205                 210                 215 gat gaa cga cta aat aga atg ttt cag acg cct cat tca gta cag tgg      846
Asp Glu Arg Leu Asn Arg Met Phe Gln Thr Pro His Ser Val Gln Trp
            220                 225                 230 atg cga cct gga act caa gat ggg gag tca gcg tct gac tgg ttc aat      894
Met Arg Pro Gly Thr Gln Asp Gly Glu Ser Ala Ser Asp Trp Phe Asn
        235                 240                 245 ata ttg gta ctt cat cag aat agg ata aag aca aac cct aaa agt gcc      942
Ile Leu Val Leu His Gln Asn Arg Ile Lys Thr Asn Pro Lys Ser Ala
250                 255                 260 atc aat gag cat ttc tta cca ggt tca tca gtc gcg acg tcc ctg att      990
Ile Asn Glu His Phe Leu Pro Gly Ser Ser Val Ala Thr Ser Leu Ile
265                 270                 275                 280 gat ggt gaa gca aaa cca aag cat gtt ctt ttg tta gaa atc aag gga     1038
Asp Gly Glu Ala Lys Pro Lys His Val Leu Leu Leu Glu Ile Lys Gly
                285                 290                 295 aat cag tac agg cca acc aaa ata cct ctg aga tct gtc aga cct ttt     1086
Asn Gln Tyr Arg Pro Thr Lys Ile Pro Leu Arg Ser Val Arg Pro Phe
            300                 305                 310 gaa tat gct gag gtt gtg ttg aaa gat gaa gca gat gtt aac tca aat     1134
Glu Tyr Ala Glu Val Val Leu Lys Asp Glu Ala Asp Val Asn Ser Asn
        315                 320                 325 gat cag gac tct gtg ctt gaa cat ttg gat aaa att gta aga aat ctg     1182
Asp Gln Asp Ser Val Leu Glu His Leu Asp Lys Ile Val Arg Asn Leu
```

```
                330                    335                    340
att gag aag agt agc caa cca act gcc agc aga tca gag ccc aaa ctt    1230
Ile Glu Lys Ser Ser Gln Pro Thr Ala Ser Arg Ser Glu Pro Lys Leu
345                    350                    355                360 cca tta gtt aga atc aag gta gat tac tct ggg ttt tca aca ata aac    1278
Pro Leu Val Arg Ile Lys Val Asp Tyr Ser Gly Phe Ser Thr Ile Asn
                365                    370                    375 cca caa cgt ttt ggt cag aag tat gtt gga aag gtc gca aac cct caa    1326
Pro Gln Arg Phe Gly Gln Lys Tyr Val Gly Lys Val Ala Asn Pro Gln
            380                    385                    390 gat att ctc att ttc tca aaa tca gca aag aag cgc cag act aca gga    1374
Asp Ile Leu Ile Phe Ser Lys Ser Ala Lys Lys Arg Gln Thr Thr Gly
        395                    400                    405 gat cac att gat gat tct gag aaa ctt cgt cct gag gaa cta aac caa    1422
Asp His Ile Asp Asp Ser Glu Lys Leu Arg Pro Glu Glu Leu Asn Gln
    410                    415                    420 caa aca atc gaa gct ctg gtc gca gag agt aac ttg aaa atg gag att    1470
Gln Thr Ile Glu Ala Leu Val Ala Glu Ser Asn Leu Lys Met Glu Ile
425                    430                    435                440 ctt ccg gtt gat gat ttg gac att gcg ttg cat gat ttt gtg aac aag    1518
Leu Pro Val Asp Asp Leu Asp Ile Ala Leu His Asp Phe Val Asn Lys
                445                    450                    455 gat gac aag atg gca ttt tat tca tgt ttg cag aga aac ctt gaa gaa    1566
Asp Asp Lys Met Ala Phe Tyr Ser Cys Leu Gln Arg Asn Leu Glu Glu
            460                    465                    470 acc agg aat aag ttg agt tct gaa gca gat aaa tcc aaa ttt gag gaa    1614
Thr Arg Asn Lys Leu Ser Ser Glu Ala Asp Lys Ser Lys Phe Glu Glu
        475                    480                    485 gaa gat ata ata gtc aaa gtt ggc gag tgc atg cag gaa cgc gtt aag    1662
Glu Asp Ile Ile Val Lys Val Gly Glu Cys Met Gln Glu Arg Val Lys
    490                    495                    500 gaa agg tct ctg cac tct aag gac ggc aca cgt ttg aca aca ggc tct    1710
Glu Arg Ser Leu His Ser Lys Asp Gly Thr Arg Leu Thr Thr Gly Ser
505                    510                    515                520 cac aac ttg gtg ttt aat tat ctg agc ctt aat atc ttt tct ttt tgt    1758
His Asn Leu Val Phe Asn Tyr Leu Ser Leu Asn Ile Phe Ser Phe Cys
                525                    530                    535 att ttt cct ggg gct gga tac tgg aca gct agt aac tct tac aac ctt    1806
Ile Phe Pro Gly Ala Gly Tyr Trp Thr Ala Ser Asn Ser Tyr Asn Leu
            540                    545                    550 taactaggat actggaggta aatcttttac agctcaaagc aaccagaact ccttcagtga    1866
tgatgaagac accagggaga tgcttcttgg tgcaagatca actgatgttg gacgaaaatc    1926
atctggattt actagaccct ccaaagatac tgctgatgtt gctaaacgtg gtacttccaa    1986
aagaggcagg ggaagaggca ccagttcaat gaagcagacc actcttagtt tcagccagtc    2046
aaggtcagct accgttattc gtagtgagga tgtggcttcc tctgaggagg aagcagatgc    2106
aaatgaagtt gttgaaaatt cagaagagga gagtgcgcaa caagttggac gtaaaagagc    2166
agctcctagg ggtagaggta gaggtagagg cggaggttcc actgcaaaga ggggcgaaa    2226 aacagatatt gcttccatgc aaaatatgat gagcaaagat gatgatgatt cagaagatga    2286
accgccaaag aaaactcctc gggtcaccag gaactatggc gctgtcagga ggagatgacc    2346
ctttaaggag ttcttgctca tgagagttat aggctaggtg ttttgtcttg taagttgga    2406 agagccgacg tgtttttatc aaccttgacg tcgaccagtt tgcgttgccg tgaactgact    2466
gtaccttgta cacgcccgaa tgtaacggat ttttgggatt tatacatcct tgtagctgct    2526
taaattccag cgattgctgt caaatgaact tcgggaaaaa aaaaaaaaaa aaaaaaaaa    2586
```
aaaaaaaaaa a                                                          2597

<210> SEQ ID NO 2
<211> LENGTH: 552
<212> TYPE: PRT
<213> ORGANISM: Zea mays

<400> SEQUENCE: 2

Met Val Gly Phe Cys Ser Ala Leu Asp Leu Gln Gln Arg Ile Gly Leu
1               5                   10                  15

Ala Asn Thr Leu Ser Ser Gly Ser Met Ser Glu Pro Ala Gln Pro Ser
            20                  25                  30

Gly Gly Glu Gly Asp Val Asn Thr Leu Arg Ile Leu Val Ala Thr Asp
        35                  40                  45

Cys His Leu Gly Tyr Met Glu Lys Asp Glu Ile Arg Arg Phe Asp Ser
    50                  55                  60

Phe Gln Ala Phe Glu Glu Ile Cys Ala Leu Ala Asp Lys Asn Lys Val
65                  70                  75                  80

Asp Phe Ile Leu Leu Gly Gly Asp Leu Phe His Glu Asn Lys Pro Ser
                85                  90                  95

Arg Ser Thr Leu Val Lys Thr Ile Glu Ile Leu Arg Arg Tyr Cys Leu
            100                 105                 110

Asn Asp Gln Pro Val Lys Phe Gln Val Val Ser Asp Gln Thr Val Asn
        115                 120                 125

Phe Pro Asn Arg Phe Gly Lys Val Asn Tyr Glu Asp Pro Asn Phe Asn
    130                 135                 140

Val Gly Leu Pro Val Phe Thr Ile His Gly Asn His Asp Asp Pro Ala
145                 150                 155                 160

Gly Val Asp Asn Leu Ser Ala Ile Asp Ile Leu Ser Ala Cys Asn Leu
                165                 170                 175

Val Asn Tyr Phe Gly Lys Met Asp Leu Gly Ser Gly Val Gly Gln
            180                 185                 190

Ile Ala Val Tyr Pro Val Leu Val Lys Lys Gly Met Thr Ser Val Ala
        195                 200                 205

Leu Tyr Gly Leu Gly Asn Ile Arg Asp Glu Arg Leu Asn Arg Met Phe
    210                 215                 220

Gln Thr Pro His Ser Val Gln Trp Met Arg Pro Gly Thr Gln Asp Gly
225                 230                 235                 240

Glu Ser Ala Ser Asp Trp Phe Asn Ile Leu Val Leu His Gln Asn Arg
                245                 250                 255

Ile Lys Thr Asn Pro Lys Ser Ala Ile Asn Glu His Phe Leu Pro Gly
            260                 265                 270

Ser Ser Val Ala Thr Ser Leu Ile Asp Gly Glu Ala Lys Pro Lys His
        275                 280                 285

Val Leu Leu Leu Glu Ile Lys Gly Asn Gln Tyr Arg Pro Thr Lys Ile
    290                 295                 300

Pro Leu Arg Ser Val Arg Pro Phe Glu Tyr Ala Glu Val Leu Lys
305                 310                 315                 320

Asp Glu Ala Asp Val Asn Ser Asn Asp Gln Asp Ser Val Leu Glu His
                325                 330                 335

Leu Asp Lys Ile Val Arg Asn Leu Ile Glu Lys Ser Ser Gln Pro Thr
            340                 345                 350

Ala Ser Arg Ser Glu Pro Lys Leu Pro Leu Val Arg Ile Lys Val Asp
        355                 360                 365

```
Tyr Ser Gly Phe Ser Thr Ile Asn Pro Gln Arg Phe Gly Gln Lys Tyr
    370                 375                 380

Val Gly Lys Val Ala Asn Pro Gln Asp Ile Leu Ile Phe Ser Lys Ser
385                 390                 395                 400

Ala Lys Lys Arg Gln Thr Thr Gly Asp His Ile Asp Asp Ser Glu Lys
                405                 410                 415

Leu Arg Pro Glu Glu Leu Asn Gln Gln Thr Ile Glu Ala Leu Val Ala
            420                 425                 430

Glu Ser Asn Leu Lys Met Glu Ile Leu Pro Val Asp Asp Leu Asp Ile
        435                 440                 445

Ala Leu His Asp Phe Val Asn Lys Asp Lys Met Ala Phe Tyr Ser
    450                 455                 460

Cys Leu Gln Arg Asn Leu Glu Glu Thr Arg Asn Lys Leu Ser Ser Glu
465                 470                 475                 480

Ala Asp Lys Ser Lys Phe Glu Glu Asp Ile Ile Val Lys Val Gly
                485                 490                 495

Glu Cys Met Gln Glu Arg Val Lys Glu Arg Ser Leu His Ser Lys Asp
            500                 505                 510

Gly Thr Arg Leu Thr Thr Gly Ser His Asn Leu Val Phe Asn Tyr Leu
        515                 520                 525

Ser Leu Asn Ile Phe Ser Phe Cys Ile Phe Pro Gly Ala Gly Tyr Trp
    530                 535                 540

Thr Ala Ser Asn Ser Tyr Asn Leu
545                 550

<210> SEQ ID NO 3
<211> LENGTH: 36
<212> TYPE: DNA
<213> ORGANISM: Artificial Sequence
<220> FEATURE:
<223> OTHER INFORMATION: Designed oligonucleotide based upon an adaptor
      used for cDNA library construction and poly(dT) to
      remove clones which have a poly(A) tail but no
      cDNA insert.

<400> SEQUENCE: 3
tcgacccacg cgtccgaaaa aaaaaaaaaa aaaaaa                              36

<210> SEQ ID NO 4
<211> LENGTH: 2308
<212> TYPE: DNA
<213> ORGANISM: Zea mays

<400> SEQUENCE: 4
ccgactgcca tctaggctac atggagaaag atgagatacg taggtttgat tcctttcaag     60
catttgagga gatttgcgca ttggcagata aaaataaggt ggatttttata cttctcggtg   120 gtgatctatt ccatgagaac aagccgtcac gctcaaccct ggtaaaaacg attgagattc   180
tacggcgcta ctgcctaaat gatcaacctg tgaagttcca ggttgtcagt gatcagacag   240
ttaactttcc aaacaggttt ggtaaggtaa attatgaaga cccaaacttt aacgttggtc   300
tgcctgtgtt caccattcat ggaaatcatg atgaccctgc tggagtggat aatctctctg   360
ctatcgatat tctttcggct tgcaatcttg taaattattt tggaaagatg gaccttggtg   420
gctctggcgt tggtcagata gcagtttatc ctgtacttgt aaaaaagggc atgacttcag   480
ttgcactgta tggtcttgga aacattagag atgaacgact aaatagaatg tttcagacgc   540
ctcattcagt acagtggatg cgacctggaa ctcaagatgg ggagtcagcg tctgactggt   600
```

```
tcaatatatt ggtacttcat cagaatagga taaagacaaa ccctaaaagt gccatcaatg      660
agcatttctt accaggttca tcagtcgcga cgtccctgat tgatggtgaa gcaaaaccaa      720
agcatgttct tttgttagaa atcaagggaa atcagtacag gccaaccaaa atacctctga      780
gatctgtcag acctttgaa tatgctgagg ttgtgttgaa agatgaagca gatgttaact      840
caaatgatca ggactctgtg cttgaacatt tggataaaat tgtaagaaat ctgattgaga      900
agagtagcca accaactgcc agcagatcag agcccaaact tccattagtt agaatcaagg      960
tagattactc tgggttttca acaataaacc cacaacgttt tggtcagaag tatgttggaa     1020
aggtcgcaaa ccctcaagat attctcattt tctcaaaatc agcaaagaag cgccagacta     1080
caggagatca cattgatgat tctgagaaac ttcgtcctga ggaactaaac caacaaacaa     1140
tcgaagctct ggtcgcagag agtaacttga aaatggagat tcttccggtt gatgatttgg     1200
acattgcgtt gcatgatttt gtgaacaagg atgacaagat ggcattttat tcatgtttgc     1260
agagaaacct tgaagaaacc aggaataagt tgagttctga agcagataaa tccaaatttg     1320
aggaagaaga tataatagtc aaagttggcg agtgcatgca ggaacgcgtt aaggaaaggt     1380
ctctgcactc taaggacggc acacgtttga caacaggctc tcacaacttg gtgtttaatt     1440
atctgagcct taatatcttt tcttttttgta tttttcctgg ggctggatac tggacagcta     1500
gtaactctta caacctttaa ctaggatact ggaggtaaat cttttacagc tcaaagcaac     1560
cagaactcct tcagtgatga tgaagacacc agggagatgc ttcttggtgc aagatcaact     1620
gatgttggac gaaaatcatc tggatttact agaccctcca aagatactgc tgatgttgct     1680
aaacgtggta cttccaaaag aggcagggga agaggcacca gttcaatgaa gcagaccact     1740
cttagtttca gccagtcaag gtcagctacc gttattcgta gtgaggatgt ggcttcctct     1800
gaggaggaag cagatgcaaa tgaagttgtt gaaaattcag aagaggagag tgcgcaacaa     1860
gttggacgta aaagagcagc tcctagggt agaggtagag gtagaggcgg aggttccact     1920
gcaaagaggg ggcgaaaaac agatattgct tccatgcaaa atatgatgag caaagatgat     1980
gatgattcag aagatgaacc gccaaagaaa actcctcggg tcaccaggaa ctatggcgct     2040
gtcaggagga gatgacccctt taaggagttc ttgctcatga gagttatagg ctaggtgttt     2100
tgtcttgtaa agttggaaga gccgacgtgt ttatcaac cttgacgtcg accagtttgc     2160
gttgccgtga actgactgta ccttgtacac gcccgaatgt aacggatttt tgggatttat     2220
acatccttgt agctgcttaa attccagcga ttgctgtcaa atgaacttcg ggaaaaaaaa     2280
aaaaaaaaaa aaaaaaaaa aaaaaaa                                         2308
```

<210> SEQ ID NO 5
<211> LENGTH: 396
<212> TYPE: DNA
<213> ORGANISM: Zea mays

<400> SEQUENCE: 5

```
tcgacccacg cgtccggccg gcccttctct tcccttgctg ctgtgcgaac ccgagcgccc       60
aaacctgaac ttaagctatt tggggctact tgtatttgga aaaatatat cgggtccttt      120 actggtccgc cggtgttatt ttaacttatg aaatggttgg ttttgcagt gcattagatt      180 tacagcaacg gattggtttg gccaacacgt tgagttcagg ttcaatgtct gaaccagcac      240
aacctagtgg agggggaagt gatgtcaaca cgctcctaat acttgtagca accgactgcc      300
atctaggcta catggagaaa gatgagatac gtaggtttga ttcctttcaa gcatttgagg      360
```

```
agatttgcgc attggcagat aaaaataagg tggatt                                    396

<210> SEQ ID NO 6
<211> LENGTH: 36
<212> TYPE: DNA
<213> ORGANISM: Artificial Sequence
<220> FEATURE:
<223> OTHER INFORMATION: M13R synthetic primer

<400> SEQUENCE: 6
agcggataac aatttcacac aggaaacagc tatgac                                    36

<210> SEQ ID NO 7
<211> LENGTH: 20
<212> TYPE: DNA
<213> ORGANISM: Artificial Sequence
<220> FEATURE:
<223> OTHER INFORMATION: R1 synthetic primer

<400> SEQUENCE: 7
cttattttta tctgccaatg                                                      20

<210> SEQ ID NO 8
<211> LENGTH: 25
<212> TYPE: DNA
<213> ORGANISM: Artificial Sequence
<220> FEATURE:
<223> OTHER INFORMATION: T7 synthetic primer

<400> SEQUENCE: 8
taatacgact cactataggg cgaat                                                25

<210> SEQ ID NO 9
<211> LENGTH: 20
<212> TYPE: DNA
<213> ORGANISM: Artificial Sequence
<220> FEATURE:
<223> OTHER INFORMATION: R2 synthetic primer

<400> SEQUENCE: 9
gcgtgacggc ttgttctcat                                                      20
```

MRE11 ORTHOLOGUE AND USES THEREOF

CROSS-REFERENCE TO RELATED APPLICATIONS

This application is a divisional application of U.S. application Ser. No. 09/835,654 filed Apr. 16, 2001, now U.S. Pat. No. 6,646,182, and claims the benefit of U.S. application Ser. No. 60/198,570 filed Apr. 19, 2000, all of which are herein incorporated by reference.

TECHNICAL FIELD

The present invention relates generally to plant molecular biology. More specifically, it relates to nucleic acids and methods for modulating their expression in plants.

BACKGROUND OF THE INVENTION

In 1993, Ajimura et al. isolated a temperature sensitive mutant of *S. cerevisiae* that was shown to be defective in initiation of meiotic recombination. This mutant, mre11-1, was sensitive to the radiomimetic agent methyl methanesulfonate (MMS) and showed a 10-fold increase in the level of mitotic recombination (Ajimura et al., *Genetics* 133: 51–66,1993). Based on these properties, the MRE11 gene has been classified as belonging to same epistasis group as RAD50. A null mutant of MRE11 is unable to initiate meiosis, rendering the spores non-viable. The Mre11 protein has been shown to interact with the Rad50 protein to initiate double strand breaks in meiotic recombination (Johzuka K. and Ogawa H., *Genetics* 139:1521–1532, 1995). A new mutant allele, mre11S, was isolated and shown to block processing but not formation of double strand breaks (Nairz K. and Klein F., *Genes and Dev.* 11:2272–2290, 1997). Another mutant Mre11 allele which has been characterized, mre11-58, has been shown to contain two amino acid changes from the wild type protein. Interestingly, unlike mre11 null mutants, mre11-58 was proficient in formation of double strand breaks, but defective in processing of the DNA ends, indicating the involvement of Mre11 protein in exonucleolytic processing of double strand breaks during meiosis (Tsubouchi H. and Ogawa H., *Mol. Cell. Biol.* 18:260–268, 1998). This 3' to 5' exonuclease activity of Mre11 on double-stranded DNA either by itself, or in complex with Rad50 and Xrs2/p95 has been clearly established by two different groups (Paull T. and Gellert M., *Mol. Cell* 1:969–979,1998; Trujillo et al., *J Biol Chem* 273: 21447–21450,1998). The exonuclease activity is observed only in the presence of $Mn^{++}$. Mre11 also exhibits $Mn^{++}$-dependent endonuclease activity on ssDNA (Trujillo et al., *J Biol Chem* 273:21447–21450, 1998) as well as on hairpin loops formed during V(D)J recombination (Paull T. and Gellert M., *Mol. Cell* 1:969–979, 1998).

The involvement of the MRE11/RAD50/XRS2 group of genes in non-homologous end joining (also known as non-homologous or illegitimate recombination) has also been well documented (Moore J K and Haber J E, *Mol. Cell Biol.* 16:2164–2173, 1996; Tsukamoto et al., *Genetics* 142:383–391, 1996; Wilson et al., *Nucleic Acid Res* 27:2655–2661, 1999; Lewis et al., *Genetics* 152:1513–1529, 1999). Furthermore, Mre11, along with Rad50 and Xrs2/p95, plays a critical role in the DNA damage response, as well as G2/M cell arrest following DNA damage, and DNA repair (Dolganov et al., *Mol Cell Biol.* 16: 4832–4841,1996; Carney et al., *Cell* 93:477–486,1998; Lee et al., *Cell* 94:399–409, 1998). Recently, Mre11 has been shown to be essential for the maintenance of chromosomal DNA (Yamaguchi-Iwai et al., *Embo J.* 18:6619–6629, 1999).

In summary, MRE11 is an important gene involved in meiotic and mitotic recombination, as well as homologous and non-homologous recombination. Thus, this single protein participates in multiple pathways that are often competing with each other such as double-strand break (DSB) formation in meiosis and DSB repair (via non-homologous end joining pathway) in mitosis. A very recent study by Furuse et al. employed two specific mutants of yeast Mre11 to elucidate this phenomenon (Furuse et al., *EMBO J.* 17:6412–6425; 1998). A point mutation in Mre11 (Asp16Ala) completely abolished the nuclease activity, without any change in DNA binding activity. This mutation also conferred MMS sensitivity to mitotic cells and caused them to accumulate unprocessed DSBs during meiosis. However, another mutant carrying a deletion of 49 C-terminal amino acids had almost wild-type levels of nuclease activity but reduced DNA binding activity. The mitotic phenotypes of this mutant were essentially unchanged, but the meiotic DSB formation was reduced dramatically. These results indicate the presence of two distinct functional domains on the Mre11 protein, an N-terminal region specifically involved in mitotic functions and a C-terminal 49 amino acid domain involved in the meiotic DSB formation. Thus, interactions of different domains with other proteins (such as Rad50 and Xrs2/P95) may be an underlying mechanism for the distinct roles of Mre11 in meiosis and mitosis (Usui et al., *Cell* 95:705–716, 1998). Whatever mechanisms may be involved, it is clear that either null or the N-terminal nuclease domain mutants of Mre11 are deficient in non-homologous end-joining.

Homologues of yeast MRE11 have been isolated from *S. pombe* (Tavassoli et al., *Nucleic Acid Res.* 23:383–388, 1995), human (Petrini J H et al., *Genomics* 29:80–86, 1995; Chamankhah et al., *Gene* 225:107–116, 1998), and mouse (Xiao Y and Weaver D, *Nucleic Acid Res.* 25:2985–2991, 1997). Similarly, cDNA sequences encoding yeast Mre11-like proteins from *Drosophila* (Accession No. AF132144) *Xenopus* (Accession No. AF134569), *Coprinus* (Accession No. AF178433) and *Arabidopsis* (Accession No. AJ243822) have been deposited in the Genbank database.

Control of non-homologous end joining as well as mitotic and meiotic recombination by the modulation of Mre11, provides the means to modulate the efficiency with which heterologous nucleic acids are incorporated into the genomes of a target plant cell. Control of these processes has important implications in the creation of novel recombinantly engineered crops such as maize. The present invention provides this and other advantages.

SUMMARY OF THE INVENTION

The present invention teaches a full-length cDNA for a Mre11 orthologue. The protein shares homology with the published Mre11 sequences. For example, the N-terminal Asp16 residue from the yeast Mre11 sequence which is involved in nuclease function is conserved in the maize protein as are several motifs found in many members of the phosphodiesterase/Mre11 gene family (Example 4). Generally, it is the object of the present invention to provide nucleic acids and proteins relating to Mre11. It is an object of the present invention to provide transgenic plants comprising the nucleic acids of the present invention, and methods for modulating, in a transgenic plant, expression of the nucleic acids of the present invention. It is also an object of the present invention to provide methods for increasing transformation efficiency.

Therefore, in one aspect the present invention relates to an isolated nucleic acid comprising a member selected from the group consisting of (a) a polynucleotide having a specified sequence identity to a polynucleotide encoding a polypeptide of the present invention; (b) a polynucleotide which is complementary to the polynucleotide of (a); and, (c) a polynucleotide comprising a specified number of contiguous nucleotides from a polynucleotide of (a) or (b). The isolated nucleic acid can be DNA.

In other aspects the present invention relates to: 1) recombinant expression cassettes, comprising a nucleic acid of the present invention operably linked to a promoter, 2) a host cell into which has been introduced the recombinant expression cassette, and 3) a transgenic plant comprising the recombinant expression cassette. The host cell and plant are optionally from maize, wheat, rice, or soybean. The present invention also provides transgenic seed from the transgenic plant.

In a further aspect, the present invention relates to an isolated protein comprising a polypeptide having a specified number of contiguous amino acids encoded by an isolated nucleic acid of the present invention.

In a further aspect, the present invention relates to a polynucleotide amplified from a Zea mays nucleic acid library using primers which selectively hybridize, under stringent hybridization conditions, to loci within polynucleotides of the present invention.

In another aspect, the present invention relates to an isolated nucleic acid comprising a polynucleotide of specified length which selectively hybridizes under stringent conditions to a polynucleotide of the present invention, or a complement thereof. In some embodiments, the isolated nucleic acid is operably linked to a promoter.

In another aspect, the present invention relates to a recombinant expression cassette comprising a nucleic acid amplified from a library as referred to supra, wherein the nucleic acid is operably linked to a promoter. In some embodiments, the present invention relates to a host cell transfected with this recombinant expression cassette. In some embodiments, the present invention relates to a protein of the present invention that is produced from this host cell.

DETAILED DESCRIPTION OF THE INVENTION

Overview

A. Nucleic Acids and Protein of the Present Invention

Unless otherwise stated, the polynucleotide and polypeptide sequences identified in Table 1 represent polynucleotides and polypeptides of the present invention. Table 1 cross-references these polynucleotide and polypeptides to their gene name. A nucleic acid of the present invention comprises a polynucleotide of the present invention. A protein of the present invention comprises a polypeptide of the present invention.

Table 2 further provides a calculation of the percent identity/similarity of the referenced polynucleotide/polypeptide sequences to homologues identified using methods such as the one disclosed in Example 7.

TABLE 1

| Gene | Polynucleotide SEQ ID NO. | Polypeptide SEQ ID NO. |
|---|---|---|
| Zea mays Mre11 Orthologue | SEQ ID NO: 1 | SEQ ID NO: 2 |

TABLE 2

| Reference SEQ ID NO. | Homologue Species | Homologue Accession No. | % Identity to the reference sequence |
|---|---|---|---|
| SEQ ID NO: 1 | Arabidopsis thaliana | AJ243822 | 59.3% |
| SEQ ID NO: 2 | Arabidopsis thaliana | Q9XGM2 | 77.2% |

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges recited within the specification are inclusive of the numbers defining the range and include each integer within the defined range. Amino acids may be referred to herein by either their commonly known three letter symbols or by the one-letter symbols recommended by the IUPAC-IUBMB Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5$^{th}$ edition, 1993). The terms defined below are more fully defined by reference to the specification as a whole. Section headings provided throughout the specification are not limitations to the various objects and embodiments of the present invention.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The term "antibody" includes reference to antigen binding forms of antibodies (e.g., Fab, F(ab)$_2$). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "antigen" includes reference to a substance to which an antibody can be generated and/or to which the antibody is specifically immunoreactive. The specific immunoreactive sites within the antigen are known as epitopes or antigenic determinants. These epitopes can be a linear array of monomers in a polymeric composition—such as amino acids in a protein—or consist of or comprise a more complex secondary or tertiary structure. Those of skill will recognize that all immunogens (i.e., substances capable of eliciting an immune response) are antigens; however some antigens, such as haptens, are not immunogens but may be made immunogenic by coupling to a carrier molecule. An antibody immunologically reactive with a particular antigen can be generated in vivo or by recombinant methods such as selection of libraries of recombinant antibodies in phage or similar vectors. See, e.g., Huse et al., *Science* 246:1275–1281 (1989); and Ward et al., *Nature* 341:544–546 (1989); and Vaughan et al., *Nature Biotech.* 14:309–314 (1996).

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

As used herein, "chromosomal region" includes reference to a length of a chromosome that may be measured by reference to the linear segment of DNA that it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17:477–498 (1989)). Thus, the maize preferred codon for a particular amino acid may be derived from known gene sequences from maize. Maize codon usage for 28 genes from maize plants is listed in Table 4 of Murray et al., supra.

As used herein "full-length sequence" in reference to a specified polynucleotide or its encoded protein means having the entire amino acid sequence of, a native (non-synthetic), endogenous, biologically (e.g., structurally or catalytically) active form of the specified protein. Methods to determine whether a sequence is full-length are well known in the art including such exemplary techniques as northern or western blots, primer extension, S1 protection, and ribonuclease protection. See, e.g., *Plant Molecular Biology. A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN<u>AUG</u>G, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by human intervention.

By "host cell" is meant a cell which contains a vector and supports the replication and/or expression of the vector. Host cells may be prokaryotic cells such as *E. coli*, or eukaryotic cells such as yeast, insect, amphibian, or mammalian cells. Host cells can also be monocotyledonous or dicotyledonous plant cells, an example of a monocotyledonous host cell is a maize host cell.

The term "hybridization complex" includes reference to a duplex nucleic acid structure formed by two single-stranded nucleic acid sequences selectively hybridized with each other.

The term "introduced" includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA). The term includes such nucleic acid introduction means as "transfection", "transformation" and "transduction".

The term "isolated" refers to material, such as a nucleic acid or a protein, which is substantially free from components that normally accompany or interact with it as found in its naturally occurring environment. The isolated material optionally comprises material not found with the material in its natural environment, or if the material is in its natural environment, the material has been synthetically (non-naturally) altered by human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, "nucleic acid" includes reference to a deoxyribonucleotide or ribonucleotide polymer, or chimeras thereof, in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism, tissue, or of a cell type from that organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2nd ed., Vol. 1–3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen, and microspores. The class of plants which can be used in the methods of the invention include both monocotyledonous and dicotyledonous plants. An example of a monocotyledonous plant is *Zea mays*.

As used herein, "polynucleotide" includes reference to a deoxyribopolynucleotide, ribopolynucleotide, or chimeras or analogs thereof that have the essential nature of a natural deoxy- or ribo-nucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms also apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of human intervention. The term "recombinant" as used herein does not encompass the alteration of the cell or vector by naturally occurring events (e.g., spontaneous mutation, natural transformation/transduction/transposition) such as those occurring without human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "stringent conditions" or "stringent hybridization conditions" includes reference to conditions under which a probe will selectively hybridize to its target sequence, to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267–284 (1984): $T_m = 81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. Hybridization and/or wash conditions can be applied for at least 10, 30, 60, 90, 120, or 240 minutes. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel et al., Eds., Greene Publishing and Wiley-Interscience, New York (1995).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in introduction of a polynucleotide of the present invention into a host cell. Vectors are often replicons. Expression vectors permit transcription of a nucleic acid inserted therein.

The following terms are used to describe the sequence relationships between a polynucleotide/polypeptide of the present invention with a reference polynucleotide/polypeptide: (a) "reference sequence", (b) "comparison window", (c) "sequence identity", and (d) "percentage of sequence identity".

(a) As used herein, "reference sequence" is a defined sequence used as a basis for sequence comparison with a polynucleotide/polypeptide of the present invention. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids residues in length, and optionally can be 30, 40, 50, 100, or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG®, Accelrys, San Diego, Calif.); the CLUSTAL program is well described by Higgins and Sharp, *Gene* 73:237–244 (1988); Higgins and Sharp, *CABIOS* 5:151–153 (1989); Corpet et al., *Nucleic Acids Research* 16:10881–90 (1988); Huang et al., *Computer Applications in the Biosciences* 8:155–65 (1992), and Pearson et al., *Methods in Molecular Biology* 24:307–331 (1994).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel et al., Eds., Greene Publishing and Wiley-Interscience, New York (1995); Altschul et al., *J. Mol. Biol.* 215:403–410 (1990); and, Altschul et al., *Nucleic Acids Res.* 25:3389–3402 (1997).

Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5877 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149–163 (1993)) and XNU (Claverie and States, *Comput. Chem.* 17:191–201 (1993)) low-complexity filters can be employed alone or in combination.

Unless otherwise stated, nucleotide and protein identity/similarity values provided herein are calculated using GAP (Version 10, GCG®, Accelrys, San Diego, Calif.) under default values.

GAP (Global Alignment Program) can also be used to compare a polynucleotide or polypeptide of the present invention with a reference sequence. GAP uses the algorithm of Needleman and Wunsch (*J. Mol. Biol.* 48:443–453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package (GCG®, Accelrys, San Diego, Calif.) for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can each independently be: 0, 1, 2, 3, 4, 5, 6, 7, 8, 9, 10, 15, 20, 30, 40, 50, 60 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package (GCG®, Accelrys, San Diego, Calif.) is BLOSUM62 (see Henikoff & Henikoff (1989) *Proc. Natl. Acad. Sci. USA* 89:10915).

Multiple alignment of the sequences can be performed using the CLUSTAL method of alignment (Higgins and Sharp (1989) *CABIOS.* 5:151–153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.* 4:11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Utilities

The present invention provides, among other things, compositions and methods for modulating (i.e., increasing or decreasing) the level of polynucleotides and polypeptides of the present invention in plants. In particular, the polynucleotides and polypeptides of the present invention can be expressed temporally or spatially, e.g., at developmental stages, in tissues, and/or in quantities, which are uncharacteristic of non-recombinantly engineered plants. Thus the present invention provides utility in such exemplary applications as in the regulation of DNA recombination and repair and increasing transformation efficiency.

The present invention also provides isolated nucleic acids comprising polynucleotides of sufficient length and complementarity to a polynucleotide of the present invention to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms), orthologs, or paralogs of the gene, or for site directed mutagenesis in eukaryotic cells (see, e.g., U.S. Pat. No. 5,565,350). The isolated nucleic acids of the present invention can also be used for recombinant expression of their encoded polypeptides, or for use as immunogens in the preparation and/or screening of antibodies. The isolated nucleic acids of the present invention can also be employed for use in sense or antisense suppression of one or more genes of the present invention in a host cell, tissue, or plant. Attachment of chemical agents which bind, intercalate, cleave and/or crosslink to the isolated nucleic acids of the present invention can also be used to modulate transcription or translation.

The present invention also provides isolated proteins comprising a polypeptide of the present invention (e.g., preproenzyme, proenzyme, or enzymes). The present invention also provides proteins comprising at least one epitope from a polypeptide of the present invention. The proteins of the present invention can be employed in assays for enzyme agonists or antagonists of enzyme function, or for use as immunogens or antigens to obtain antibodies specifically immunoreactive with a protein of the present invention. Such antibodies can be used in assays for expression levels, for identifying and/or isolating nucleic acids of the present invention from expression libraries, for identification of homologous polypeptides from other species, or for purification of polypeptides of the present invention.

The isolated nucleic acids and polypeptides of the present invention can be used over a broad range of plant types, particularly monocots such as the species of the family Gramineae including Hordeum, Secale, Oryza, Triticum, Sorghum (e.g., S. bicolor) and Zea (e.g., Z. mays), and dicots such as Glycine.

The isolated nucleic acid and proteins of the present invention can also be used in species from the genera: Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browallia, Pisum, Phaseolus, Lolium, and Avena.

Nucleic Acids

The mre-11 gene encodes a protein involved in DNA repair and recombination. It was initially isolated as a mutant deficient in initiation of meiotic recombination and has been shown to have 3' to 5' exonuclease activity. It is involved in non-homologous end-joining and the DNA damage response. As such it is expected that regulation of mre11 will have useful application to increase transformation efficiency.

The present invention provides, among other things, isolated nucleic acids of RNA, DNA, and analogs and/or chimeras thereof, comprising a polynucleotide of the present invention.

A polynucleotide of the present invention is inclusive of:

(a) a polynucleotide encoding a polypeptide of SEQ ID NO: 2 including exemplary polynucleotides of SEQ ID NO: 1; the polynucleotide sequences of the invention also include the maize Mre11 polynucleotide sequence as contained in a plasmid deposited with American Type Culture Collection (ATCC) and assigned Accession Number PTA-1607.

(b) a polynucleotide which is the product of amplification from a Zea mays nucleic acid library using primer pairs which selectively hybridize under stringent conditions to loci within a polynucleotide selected from the polynucleotide of SEQ ID NO: 1; or the sequence as contained in the ATCC deposit assigned Accession Number PTA-1607.

(c) a polynucleotide which selectively hybridizes to a polynucleotide of (a) or (b);

(d) a polynucleotide having a specified sequence identity with polynucleotides of (a), (b), or (c);

(e) a polynucleotide encoding a protein having a specified number of contiguous amino acids from a prototype polypeptide, wherein the protein is specifically recognized by antisera elicited by presentation of the protein and wherein the protein does not detectably immunoreact to antisera which has been fully immunosorbed with the protein;

(f) complementary sequences of polynucleotides of (a), (b), (c), (d), or (e);

(g) a polynucleotide comprising at least a specific number of contiguous nucleotides from a polynucleotide of (a), (b), (c), (d), (e), or (f);

(h) an isolated polynucleotide from a full-length enriched cDNA library having the physico-chemical property of selectively hybridizing to a polynucleotide of (a), (b), (c), (d), (e), (f), or (g); and (i) an isolated polynucleotide made by the process of: 1) providing a full-length enriched nucleic acid library, 2) selectively hybridizing the polynucleotide to a polynucleotide of (a), (b), (c), (d), (e), (f), (g), or (h), thereby isolating the polynucleotide from the nucleic acid library.

The polynucleotide of SEQ ID NO: 1 is contained in a plasmid deposited with American Type Culture Collection (ATCC) on Mar. 30, 2000 and assigned Accession Number PTA-1607. American Type Culture Collection is located at 10801 University Blvd., Manassas, Va. 20110-2209, USA.

The ATCC deposit will be maintained under the terms of the Budapest Treaty on the International Recognition of the Deposit of Microorganisms for the Purposes of Patent Procedure. This deposit is provided as a convenience to those of skill in the art and is not an admission that a deposit is required under 35 U.S.C. Section 112.

A. Polynucleotides Encoding A Polypeptide of the Present Invention

As indicated in (a), above, the present invention provides isolated nucleic acids comprising a polynucleotide of the present invention, wherein the polynucleotide encodes a polypeptide of the present invention. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Thus, each silent variation of a nucleic acid which encodes a polypeptide of the present invention is implicit in each described polypeptide sequence and is within the scope of the present invention. Accordingly, the present invention includes polynucleotides of SEQ ID NO: 1, and the sequences as contained in the ATCC deposit assigned Accession Number PTA-1607, and polynucleotides encoding a polypeptide of SEQ ID NO: 2.

B. Polynucleotides Amplified from a Plant Nucleic Acid Library

As indicated in (b), above, the present invention provides an isolated nucleic acid comprising a polynucleotide of the present invention, wherein the polynucleotides are amplified, under nucleic acid amplification conditions, from a plant nucleic acid library. Nucleic acid amplification conditions for each of the variety of amplification methods are well known to those of ordinary skill in the art. The plant nucleic acid library can be constructed from a monocot such as a cereal crop. Exemplary cereals include corn, sorghum, alfalfa, canola, wheat, or rice. The plant nucleic acid library can also be constructed from a dicot such as soybean. Zea mays lines B73, PHRE1, A632, BMS-P2#10, W23, and Mo17 are known and publicly available. Other publicly known and available maize lines can be obtained from the Maize Genetics Cooperation (Urbana, Ill.). Wheat lines are available from the Wheat Genetics Resource Center (Manhattan, Kans.).

The nucleic acid library may be a cDNA library, a genomic library, or a library generally constructed from nuclear transcripts at any stage of intron processing. cDNA libraries can be normalized to increase the representation of relatively rare cDNAs. In optional embodiments, the cDNA library is constructed using an enriched full-length cDNA synthesis method. Examples of such methods include Oligo-Capping (Maruyama, K. and Sugano, S. *Gene* 138:171–174, 1994), Biotinylated CAP Trapper (Carninci et al. *Genomics* 37:327–336, 1996), and CAP Retention Procedure (Edery, E., Chu, L. L., et al. *Molecular and Cellular Biology* 15:3363–3371, 1995). Rapidly growing tissues or rapidly dividing cells are preferred for use as an mRNA source for construction of a cDNA library. Growth stages of corn is described in "How a Corn Plant Develops," Special Report No. 48, Iowa State University of Science and Technology Cooperative Extension Service, Ames, Iowa, Reprinted February 1993.

A polynucleotide of this embodiment (or subsequences thereof) can be obtained, for example, by using amplification primers which are selectively hybridized and primer extended, under nucleic acid amplification conditions, to at least two sites within a polynucleotide of the present invention, or to two sites within the nucleic acid which flank and comprise a polynucleotide of the present invention, or to a site within a polynucleotide of the present invention and a site within the nucleic acid which comprises it. Methods for obtaining 5' and/or 3' ends of a vector insert are well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego), pp. 28–38 (1990)); see also, U.S. Pat. No. 5,470,722, and *Current Protocols in Molecular Biology*, Unit 15.6, Ausubel et al., Eds., Greene Publishing and Wiley-Interscience, New York (1995); Frohman and Martin, *Techniques* 1:165 (1989).

Optionally, the primers are complementary to a subsequence of the target nucleic acid which they amplify but may have a sequence identity ranging from about 85% to 99% relative to the polynucleotide sequence which they are designed to anneal to. As those skilled in the art will appreciate, the sites to which the primer pairs will selectively hybridize are chosen such that a single contiguous nucleic acid can be formed under the desired nucleic acid amplification conditions. The primer length in nucleotides is selected from the group of integers consisting of from at least 15 to 50. Thus, the primers can be at least 15, 18, 20, 25, 30, 40, or 50 nucleotides in length. Those of skill will recognize that a lengthened primer sequence can be employed to increase specificity of binding (i.e., annealing) to a target sequence. A non-annealing sequence at the 5'end of a primer (a "tail") can be added, for example, to introduce a cloning site at the terminal ends of the amplicon.

The amplification products can be translated using expression systems well known to those of skill in the art. The resulting translation products can be confirmed as polypeptides of the present invention by, for example, assaying for the appropriate catalytic activity (e.g., specific activity and/or substrate specificity), or verifying the presence of one or more epitopes which are specific to a polypeptide of the present invention. Methods for protein synthesis from PCR derived templates are known in the art and available commercially. See, e.g., Amersham Life Sciences, Inc, Catalog '97, p.354.

C. Polynucleotides Which Selectively Hybridize to a Polynucleotide of (A) or (B)

As indicated in (c), above, the present invention provides isolated nucleic acids comprising polynucleotides of the present invention, wherein the polynucleotides selectively hybridize, under selective hybridization conditions, to a polynucleotide of sections (A) or (B) as discussed above. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library. In some embodiments, the polynucleotides are genomic or cDNA sequences isolated or otherwise complementary to a cDNA from a dicot or monocot nucleic acid library. Exemplary species of monocots and dicots include, but are not limited to: maize, canola, soybean, cotton, wheat, sorghum, sunflower, alfalfa, oats, sugar cane, millet, barley, and rice. The cDNA library comprises at least 50% to 95% full-length sequences (for example, at least 50%, 60%, 70%, 80%, 90%, or 95% full-length sequences). The cDNA libraries can be normalized to increase the representation of rare sequences. See, e.g., U.S. Pat. No. 5,482,845. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% to 80% sequence identity and can be employed to identify orthologous or paralogous sequences.

D. Polynucleotides Having a Specific Sequence Identity with the Polynucleotides of (A), (B) or (C)

As indicated in (d), above, the present invention provides isolated nucleic acids comprising polynucleotides of the present invention, wherein the polynucleotides have a specified identity at the nucleotide level to a polynucleotide as disclosed above in sections (A), (B), or (C), above. Identity can be calculated using, for example, the BLAST, CLUSTALW, or GAP algorithms under default conditions. The percentage of identity to a reference sequence is at least 50% and, rounded upwards to the nearest integer, can be expressed as an integer selected from the group of integers consisting of from 50 to 99. Thus, for example, the percentage of identity to a reference sequence can be at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%.

Optionally, the polynucleotides of this embodiment will encode a polypeptide that will share an epitope with a polypeptide encoded by the polynucleotides of sections (A), (B), or (C). Thus, these polynucleotides encode a first polypeptide which elicits production of antisera comprising antibodies which are specifically reactive to a second polypeptide encoded by a polynucleotide of (A), (B), or (C). However, the first polypeptide does not bind to antisera raised against itself when the antisera has been fully immunosorbed with the first polypeptide. Hence, the polynucleotides of this embodiment can be used to generate antibodies for use in, for example, the screening of expression libraries for nucleic acids comprising polynucleotides of (A), (B), or (C), or for purification of, or in immunoassays for, polypeptides encoded by the polynucleotides of (A), (B), or (C). The polynucleotides of this embodiment comprise nucleic acid sequences which can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5–100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT patent publication Nos. 91/17271, 91/18980, 91/19818, and 93/08278. Other systems for generating libraries of peptides have aspects of both in vitro chemical synthesis and recombinant methods. See, PCT Patent publication Nos. 92/05258, 92/14843, and 97/20078. See also, U.S. Pat. Nos. 5,658,754; and 5,643,768. Peptide display libraries, vectors, and screening kits are commercially available from such suppliers as Invitrogen (Carlsbad, Calif.).

E. Polynucleotides Encoding a Protein Having a Subsequence from a Prototype Polypeptide and Cross-Reactive to the Prototype Polypeptide As indicated in (e), above, the present invention provides isolated nucleic acids comprising polynucleotides of the present invention, wherein the polynucleotides encode a protein having a subsequence of contiguous amino acids from a prototype polypeptide of the present invention such as are provided in (a), above. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45, 50, 55, or 60, contiguous amino acids from the prototype polypeptide. Further, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The proteins encoded by polynucleotides of this embodiment, when presented as an immunogen, elicit the production of polyclonal antibodies which specifically bind to a prototype polypeptide such as but not limited to, a polypeptide encoded by the polynucleotide of (a) or (b), above. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art. Exemplary immunoassay formats include ELISA, competitive immunoassays, radioimmunoassays, Western blots, indirect immunofluorescent assays and the like.

In one assay method, fully immunosorbed and pooled antisera which is elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen. Accordingly, the proteins of the present invention embrace alelic variants, conservatively modified variants, and minor recombinant modifications to a prototype polypeptide.

A polynucleotide of the present invention optionally encodes a protein having a molecular weight as the non-glycosylated protein within 20% of the molecular weight of the full-length non-glycosylated polypeptides of the present invention. Molecular weight can be readily determined by SDS-PAGE under reducing conditions. Optionally, the molecular weight is within 15% of a full length polypeptide of the present invention, more preferably within 10% or 5%, and most preferably within 3%, 2%, or 1% of a full length polypeptide of the present invention.

Optionally, the polynucleotides of this embodiment will encode a protein having a specific enzymatic activity at least 50%, 60%, 80%, or 90% of a cellular extract comprising the native, endogenous full-length polypeptide of the present invention. Further, the proteins encoded by polynucleotides of this embodiment will optionally have a substantially similar affinity constant ($K_m$) and/or catalytic activity (i.e., the microscopic rate constant, $k_{cat}$) as the native endogenous, full-length protein. Those of skill in the art will recognize that $k_{cat}/K_m$ value determines the specificity for competing substrates and is often referred to as the specificity constant. Proteins of this embodiment can have a $k_{cat}/K_m$ value at least 10% of a full-length polypeptide of the present invention as determined using the endogenous substrate of that polypeptide. Optionally, the $k_{cat}/K_m$ value will be at least 20%, 30%, 40%, 50%, and most preferably at least 60%, 70%, 80%, 90%, or 95% the $k_{cat}/K_m$ value of the full-length polypeptide of the present invention. Determination of $k_{cat}$, $K_m$, and $k_{cat}/K_m$ can be determined by any number of means well known to those of skill in the art. For example, the initial rates (i.e., the first 5% or less of the reaction) can be determined using rapid mixing and sampling techniques (e.g., continuous-flow, stopped-flow, or rapid quenching techniques), flash photolysis, or relaxation methods (e.g., temperature jumps) in conjunction with such exemplary methods of measuring as spectrophotometry, spectrofluorimetry, nuclear magnetic resonance, or radioactive procedures. Kinetic values are conveniently obtained using a Lineweaver-Burk or Eadie-Hofstee plot.

F. Polynucleotides Complementary to the Polynucleotides of (A)–(E)

As indicated in (f), above, the present invention provides isolated nucleic acids comprising polynucleotides complementary to the polynucleotides of paragraphs A–E, above. As those of skill in the art will recognize, complementary sequences base-pair throughout the entirety of their length with the polynucleotides of sections (A)–(E) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

G. Polynucleotides Which are Subsequences of the Polynucleotides of (A)–(F)

As indicated in (g), above, the present invention provides isolated nucleic acids comprising polynucleotides which comprise at least 15 contiguous bases from the polynucleotides of sections (A) through (F) as discussed above. The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 20, 25, 30, 35, 40, 45, 50, 55, 60, 65, 70, 75, 80, 90, 100 or 200 contiguous nucleotides in length from the polynucleotides of (A)–(F). Optionally, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

Subsequences can be made by in vitro synthetic, in vitro biosynthetic, or in vivo recombinant methods. In optional embodiments, subsequences can be made by nucleic acid amplification. For example, nucleic acid primers will be constructed to selectively hybridize to a sequence (or its complement) within, or co-extensive with, the coding region.

The subsequences of the present invention can comprise structural characteristics of the sequence from which it is derived. Alternatively, the subsequences can lack certain structural characteristics of the larger sequence from which it is derived such as a poly (A) tail. Optionally, a subsequence from a polynucleotide encoding a polypeptide having at least one epitope in common with a prototype polypeptide sequence as provided in (a), above, may encode an epitope in common with the prototype sequence. Alternatively, the subsequence may not encode an epitope in common with the prototype sequence but can be used to isolate the larger sequence by, for example, nucleic acid hybridization with the sequence from which it's derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates.

H. Polynucleotides From a Full-length Enriched cDNA Library Having the Physico-Chemical Property of Selectively Hybridizing to a Polynucleotide of (A)–(G)

As indicated in (h), above, the present invention provides an isolated polynucleotide from a full-length enriched cDNA library having the physico-chemical property of selectively hybridizing to a polynucleotide of paragraphs (A), (B), (C), (D), (E), (F), or (G) as discussed above. Methods of constructing full-length enriched cDNA libraries are known in the art and discussed briefly below. The cDNA library comprises at least 50% to 95% full-length sequences (for example, at least 50%, 60%, 70%, 80%, 90%, or 95% full-length sequences). The cDNA library can be constructed from a variety of tissues from a monocot or dicot at a variety of developmental stages. Exemplary species include maize, wheat, rice, canola, soybean, cotton, sorghum, sunflower, alfalfa, oats, sugar cane, millet, barley, and rice. Methods of selectively hybridizing, under selective hybridization conditions, a polynucleotide from a full-length enriched library to a polynucleotide of the present invention are known to those of ordinary skill in the art. Any number of stringency conditions can be employed to allow for selective hybridization. In optional embodiments, the stringency allows for selective hybridization of sequences having at least 70%, 75%, 80%, 85%, 90%, 95%, or 98% sequence identity over the length of the hybridized region. Full-length enriched cDNA libraries can be normalized to increase the representation of rare sequences.

I. Polynucleotide Products Made by a cDNA Isolation Process

As indicated in (I), above, the present invention provides an isolated polynucleotide made by the process of: 1) providing a full-length enriched nucleic acid library, 2) selectively hybridizing the polynucleotide to a polynucleotide of paragraphs (A), (B), (C), (D), (E), (F), (G, or (H) as discussed above, and thereby isolating the polynucleotide from the nucleic acid library. Full-length enriched nucleic acid libraries are constructed as discussed in paragraph (G) and below. Selective hybridization conditions are as discussed in paragraph (G). Nucleic acid purification procedures are well known in the art. Purification can be conveniently accomplished using solid-phase methods; such methods are well known to those of skill in the art and kits are available from commercial suppliers such as Advanced Biotechnologies (Surrey, UK). For example, a polynucleotide of paragraphs (A)–(H) can be immobilized to a solid support such as a membrane, bead, or particle. See, e.g., U.S. Pat. No. 5,667,976. The polynucleotide product of the present process is selectively hybridized to an immobilized polynucleotide and the solid support is subsequently isolated from non-hybridized polynucleotides by methods including, but not limited to, centrifugation, magnetic separation, filtration, electrophoresis, and the like.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot such as corn, rice, or wheat, or a dicot such as soybean.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. A polynucleotide of the present invention can be attached to a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known and extensively described in the art. For a description of various nucleic acids see, for example, Stratagene Cloning Systems, Catalogs 1999 (La Jolla, Calif.); and, Amersham Life Sciences, Inc, Catalog '99 (Arlington Heights, Ill.).

A. Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library. Isolation of RNA, and construction of cDNA and genomic libraries is well known to those of ordinary skill in the art. See, e.g., *Plant Molecular Biology: A Laboratory Manual*, Clark, Ed., Springer-Verlag, Berlin (1997); and, *Current Protocols in Molecular Biology*, Ausubel et al., Eds., Greene Publishing and Wiley-Interscience, New York (1995).

A1. Construction of a cDNA Library

Construction of a cDNA library generally entails five steps. First, first strand cDNA synthesis is initiated from a poly(A)$^+$ mRNA template using a poly(dT) primer or random hexanucleotides. Second, the resultant RNA-DNA hybrid is converted into double stranded cDNA, typically by reaction with a combination of RNAse H and DNA polymerase I (or Klenow fragment). Third, the termini of the double stranded cDNA are ligated to adaptors. Ligation of the adaptors can produce cohesive ends for cloning. Fourth, size selection of the double stranded cDNA eliminates excess adaptors and primer fragments, and eliminates partial cDNA molecules due to degradation of mRNAs or the failure of reverse transcriptase to synthesize complete first strands. Fifth, the cDNAs are ligated into cloning vectors and packaged. cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel et al., Eds., Greene Publishing and Wiley-Interscience, New York (1995). cDNA synthesis kits are available from a variety of commercial vendors such as Stratagene or Pharmacia.

A2. Full-length Enriched cDNA Libraries

A number of cDNA synthesis protocols have been described which provide enriched full-length cDNA libraries. Enriched full-length cDNA libraries are constructed to comprise at least 60%, and more preferably at least 70%, 80%, 90% or 95% full-length inserts amongst clones containing inserts. The length of insert in such libraries can be at least 2, 3, 4, 5, 6, 7, 8, 9, 10 or more kilobase pairs. Vectors to accommodate inserts of these sizes are known in the art and available commercially. See, e.g., Stratagene's lambda ZAP Express (cDNA cloning vector with 0 to 12 kb cloning capacity). An exemplary method of constructing a greater than 95% pure full-length cDNA library is described by Carninci et al., *Genomics*, 37:327–336 (1996). Other methods for producing full-length libraries are known in the art. See, e.g., Edery et al., *Mol. Cell Biol.* 15(6):3363–3371 (1995); and, PCT Application WO 96/34981.

A3. Normalized or Subtracted cDNA Libraries

A non-normalized cDNA library represents the mRNA population of the tissue it was made from. Since unique clones are out-numbered by clones derived from highly expressed genes their isolation can be laborious. Normalization of a cDNA library is the process of creating a library in which each clone is more equally represented. Construction of normalized libraries is described in Ko, *Nucl. Acids. Res.* 18(19):5705–5711 (1990); Patanjali et al., *Proc. Natl. Acad. USA* 88:1943–1947 (1991); U.S. Pat. Nos. 5,482,685, 5,482,845, and 5,637,685. In an exemplary method described by Soares et al., normalization resulted in reduction of the abundance of clones from a range of four orders of magnitude to a narrow range of only 1 order of magnitude. *Proc. Natl. Acad. Sci. USA* 91:9228–9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized cDNA pool is enriched for sequences unique to that pool. See, Foote et al. in, *Plant Molecular Biology: A Laboratory Manual*, Clark, Ed., Springer-Verlag, Berlin (1997); Kho and Zarbl, *Technique* 3(2):58–63 (1991); Sive and St. John, *Nucl. Acids Res.* 16(22):10937 (1988); *Current Protocols in Molecular Biology*, Ausubel et al., Eds., Greene Publishing and Wiley-Interscience, New York (1995); and, Swaroop et al., *Nucl. Acids Res.* 19(8):1954 (1991). cDNA subtraction kits are commercially available. See, e.g., PCR-Select (Clontech, Palo Alto, Calif.).

To construct genomic libraries, large segments of genomic DNA are generated by fragmentation, e.g. using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook, et al., *Molecular Cloning: A Laboratory Manual*, 2nd Ed., Cold Spring Harbor Laboratory Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. The T4 gene 32 protein (Boehringer Mannheim) can be used to improve yield of long PCR products.

PCR-based screening methods have been described. Wilfinger et al. describe a PCR-based method in which the longest cDNA is identified in the first step so that incomplete clones can be eliminated from study. *Bio Techniques* 22(3): 481–486 (1997). Such methods are particularly effective in combination with a full-length cDNA construction methodology, above.

A4. Construction of a Genomic Library

To construct genomic libraries, large segments of genomic DNA are generated by fragmentation, e.g. using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook et al., *Molecular Cloning: A Laboratory Manual*, 2nd Ed., Cold Spring Harbor Laboratory Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

A5. Nucleic Acid Screening and Isolation Methods

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100 percent; however, it should be understood that minor sequence variations in the probes and primers may be compensated for by reducing the stringency of the hybridization and/or wash medium.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, Sambrook, and Ausubel, as well as Mullis et al., U.S. Pat. No. 4,683,202 (1987); and, *PCR Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *Bio Techniques*, 22(3): 481–486 (1997). In that method, a primer pair is synthesized with one primer annealing to the 5' end of the sense strand of the desired cDNA and the other primer to the vector. Clones are pooled to allow large-scale screening. By this procedure, the longest possible clone is identified amongst candidate clones. Further, the PCR product is used solely as a diagnostic for the presence of the desired cDNA and does not utilize the PCR product itself. Such methods are particularly effective in combination with a full-length cDNA construction methodology, above.

B. Synthetic Methods for Constructing Nucleic Acids

The isolated nucleic acids of the present invention can also be prepared by direct chemical synthesis by methods such as the phosphotriester method of Narang et al., *Meth. Enzymol*. 68:90–99 (1979); the phosphodiester method of Brown et al., *Meth. Enzymol*. 68:109–151 (1979); the diethylphosphoramidite method of Beaucage et al., *Tetra. Lett*. 22:1859–1862 (1981); the solid phase phosphoramidite triester method described by Beaucage and Caruthers, *Tetra. Letts*. 22(20):1859–1862 (1981), e.g., using an automated synthesizer, e.g., as described in Needham-VanDevanter et al., *Nucleic Acids Res.*, 12:6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is best employed for sequences of about 100 bases or less, longer sequences may be obtained by the ligation of shorter sequences.

Recombinant Expression Cassettes

The present invention further provides recombinant expression cassettes comprising a nucleic acid of the present invention. A nucleic acid sequence coding for the desired polypeptide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterum tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, and the GRP1-8 promoter. One exemplary promoter is the ubiquitin promoter, which can be used to drive expression of the present invention in maize embryos or embryogenic callus.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter which is inducible by hypoxia or cold stress, the Hsp70 promoter which is inducible by heat stress, and the PPDK promoter which is inducible by light.

Examples of promoters under developmental control include promoters that initiate transcription only, or preferentially, in certain tissues, such as leaves, roots, fruit, seeds, or flowers. Exemplary promoters include the anther specific promoter 5126 (U.S. Pat. Nos. 5,689,049 and 5,689,051), glob-1 promoter, and gamma-zein promoter. The operation of a promoter may also vary depending on its location in the genome. Thus, an inducible promoter may become fully or partially constitutive in certain locations.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue.

Thus, in some embodiments, the nucleic acid construct will comprise a promoter, functional in a plant cell, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a cognate gene of a polynucleotide of the present invention so as to control the expression of the gene. Gene expression can be modulated under conditions suitable for plant growth so as to alter the total concentration and/or alter the composition of the polypeptides of the present invention in plant cell. Thus, the present invention provides compositions, and methods for making, heterologous promoters and/or enhancers operably linked to a native, endogenous (i.e., non-heterologous) form of a polynucleotide of the present invention.

Methods for identifying promoters with a particular expression pattern, in terms of, e.g., tissue type, cell type, stage of development, and/or environmental conditions, are well known in the art. See, e.g., *The Maize Handbook*, Chapters 114–115, Freeling and Walbot, Eds., Springer, New York (1994); *Corn and Corn Improvement*, 3$^{rd}$ edition, Chapter 6, Sprague and Dudley, Eds., American Society of Agronomy, Madison, Wis. (1988). A typical step in promoter isolation methods is identification of gene products that are expressed with some degree of specificity in the target tissue. Amongst the range of methodologies are: differential hybridization to cDNA libraries; subtractive hybridization; differential display; differential 2-D protein gel electrophoresis; DNA probe arrays; and isolation of proteins known to be expressed with some specificity in the target tissue. Such methods are well known to those of skill in the art. Commercially available products for identifying promoters are known in the art such as Clontech's (Palo Alto, Calif.) Universal GenomeWalker Kit.

For the protein-based methods, it is helpful to obtain the amino acid sequence for at least a portion of the identified protein, and then to use the protein sequence as the basis for preparing a nucleic acid that can be used as a probe to identify either genomic DNA directly, or preferably, to identify a cDNA clone from a library prepared from the target tissue. Once such a cDNA clone has been identified, that sequence can be used to identify the sequence at the 5' end of the transcript of the indicated gene. For differential hybridization, subtractive hybridization and differential display, the nucleic acid sequence identified as enriched in the target tissue is used to identify the sequence at the 5' end of the transcript of the indicated gene. Once such sequences are identified, starting either from protein sequences or nucleic acid sequences, any of these sequences identified as being from the gene transcript can be used to screen a genomic library prepared from the target organism. Methods for identifying and confirming the transcriptional start site are well known in the art.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8:4395–4405 (1988); Callis et al., *Genes Dev.* 1:1183–1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, New York (1994). The vector comprising the sequences from a polynucleotide of the present invention will typically comprise a marker gene which confers a selectable phenotype on plant cells. Typical vectors useful for expression of genes in higher plants are well known in the art and include vectors derived from the tumor-inducing (Ti) plasmid of *Agrobacterium tumefaciens* described by Rogers et al., Meth. in Enzymol., 153:253–277 (1987).

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to inhibit gene expression in plants. To accomplish this, a nucleic acid segment from the desired gene is cloned and operably linked to a promoter such that the anti-sense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy et al., *Proc. Nat'l. Acad. Sci. USA* 85:8805–8809 (1988); and Hiatt et al., U.S. Pat. No. 4,801,340.

Another method of suppression is sense suppression (i.e., co-suppression). Introduction of nucleic acid configured in the sense orientation has been shown to be an effective means by which to block the transcription of target genes. For an example of the use of this method to modulate expression of endogenous genes see, Napoli et al., *The Plant Cell* 2: 279–289 (1990) and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., *Nature* 334: 585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985)

67:785–789. Iverson and Dervan also showed sequence-specific cleavage of single-stranded DNA mediated by incorporation of a modified nucleotide which was capable of activating cleavage (*J Am Chem Soc* (1987) 109:1241–1243). Meyer, R. B., et al., *J Am Chem Soc* (1989) 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Home et al., *J Am Chem Soc* (1990) 112:2435–2437. Use of N4, N4-ethano-cytosine as an alkylating agent to crosslink to single-stranded oligonucleotides has also been described by Webb and Matteucci, *J Am Chem Soc* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681941.

Proteins

The Mre-11 protein is involved in DNA repair and recombination. The gene was initially isolated as a mutant deficient in initiation of meiotic recombination. The Mre11 protein has been shown to have 3' to 5' exonuclease activity and is involved in non-homologous end-joining and the DNA damage response. As such it is expected that modulation of Mre11 will have useful application to increase transformation efficiency, as well as DNA recombination and repair.

The isolated proteins of the present invention comprise a polypeptide having at least 10 amino acids from a polypeptide of the present invention (or conservative variants thereof such as those encoded by any one of the polynucleotides of the present invention as discussed more fully above (e.g., Table 1). The proteins of the present invention or variants thereof can comprise any number of contiguous amino acid residues from a polypeptide of the present invention, wherein that number is selected from the group of integers consisting of from 10 to the number of residues in a full-length polypeptide of the present invention. Optionally, this subsequence of contiguous amino acids is at least 15, 20, 25, 30, 35, or 40 amino acids in length, often at least 50, 60, 70, 80, or 90 amino acids in length. Further, the number of such subsequences can be any integer selected from the group consisting of from 1 to 20, such as 2, 3, 4, or 5.

The present invention further provides a protein comprising a polypeptide having a specified sequence identity/similarity with a polypeptide of the present invention. The percentage of sequence identity/similarity is an integer selected from the group consisting of from 50 to 99. Exemplary sequence identity/similarity values include 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, and 99%. Sequence identity can be determined using, for example, the GAP, CLUSTALW, or BLAST algorithms.

As those of skill will appreciate, the present invention includes, but is not limited to, catalytically active polypeptides of the present invention (i.e., enzymes). Catalytically active polypeptides have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention. Further, the proteins of the present invention will not bind to antisera raised against a polypeptide of the present invention which has been fully immunosorbed with the same polypeptide. Immunoassays for determining binding are well known to those of skill in the art. One example of an immunoassay used to determine binding is a competitive immunoassay. Thus, the proteins of the present invention can be employed as immunogens for constructing antibodies immunoreactive to a protein of the present invention for such exemplary utilities as immunoassays or protein purification techniques.

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located purification sequences. Restriction sites or termination codons can also be introduced.

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology. Vol.* 2:

*Special Methods in Peptide Synthesis, Part A.*; Merrifield et al., *J. Am. Chem. Soc.* 85:2149–2156 (1963), and Stewart et al., *Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide) are known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

Introduction of Nucleic Acids Into Host Cells

The method of introducing a nucleic acid of the present invention into a host cell is not critical to the instant invention. Transformation or transfection methods are conveniently used. Accordingly, a wide variety of methods have been developed to insert a DNA sequence into the genome of a host cell to obtain the transcription and/or translation of the sequence to effect phenotypic changes in the organism. Thus, any method which provides for effective introduction of a nucleic acid may be employed.

A. Plant Transformation

A nucleic acid comprising a polynucleotide of the present invention is optionally introduced into a plant. Generally, the polynucleotide will first be incorporated into a recombinant expression cassette or vector. Isolated nucleic acid acids of the present invention can be introduced into plants according to techniques known in the art. Techniques for transforming a wide variety of higher plant species are well known and described in the technical, scientific, and patent literature. Suitable methods of transforming plant cells include microinjection (Crossway et al. (1986) *Biotechniques* 4:320–334), electroporation (Riggs et al (1986) *Proc. Natl. Acad. Sci. USA* 83:5602–5606, *Agrobacterium* mediated transformation (see for example, Zhao et al. U.S. Pat. No. 5,981,840; U.S. Pat. No. 5,563,055), direct gene transfer (Paszkowski et al. (1984) *EMBO J.* 3:2717–2722), and ballistic particle acceleration (see, for example, Sanford et al. U.S. Pat. No. 4,945,050; Tomes et al. "Direct DNA Transfer into Intact Plant Cells via Microprojectile Bombardment" In Gamborg and Phillips (Eds.) *Plant Cell, Tissue and Organ Culture: Fundamental Methods*, Springer-Verlag, Berlin (1995); and McCabe et al. (1988) *Biotechnology* 6:923–926. Also see, Weissinger et al. (1988) *Annual Rev. Genet.* 22:421–477; Sanford et al. (1987) *Particulate Science and Technology* 5:27–37 (onion); Christou et al. (1988) *Plant Physiol.* 87:671–674 (soybean); Datta et al. (1990) *Biotechnology* 8:736–740 (rice); Klein et al. (1988) *Proc. Natl. Acad. Sci. USA* 85:43054309 (maize); Klein et al. (1988) *Biotechnology* 6:559–563 (maize); Klein et al. (1988) *Plant Physiol.* 91:440444 (maize); Fromm et al. (1990) *Biotechnology* 8:833–839 (maize); Hooykaas-Van Slogteren & Hooykaas (1984) *Nature (London)* 311:763–764; Bytebier et al. (1987) *Proc. Natl. Acad. Sci. USA* 84:5345–5349 (Liliaceae); De Wet et al. (1985) In *The Experimental Manipulation of Ovule Tissues* ed. G. P. Chapman et al. pp. 197–209. Longman, N.Y. (pollen); Kaeppler et al. (1990) *Plant Cell Reports* 9:415–418; Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255; and Christou and Ford (1995) *Annals of Botany* 75:745–750 (maize via *Agrobacterium tumefaciens*) all of which are herein incorporated by reference.

The cells which have been transformed may be grown into plants in accordance with conventional ways. See, for example, McCormick et al. (1986) *Plant Cell Reports*, 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

B. Transfection of Prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Transgenic Plant Regeneration

Plant cells which directly result or are derived from the nucleic acid introduction techniques can be cultured to regenerate a whole plant which possesses the introduced genotype. Such regeneration techniques often rely on manipulation of certain phytohormones in a tissue culture growth medium. Plants cells can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillan Publishing Company, New York, pp. 124–176 (1983); and Binding, *Regeneration of Plants, Plant Protoplasts*, CRC Press, Boca Raton, pp. 21–73 (1985).

The regeneration of plants from either single plant protoplasts or various explants is well known in the art. See, for example, *Methods for Plant Molecular Biology*, A. Weissbach and H. Weissbach, Eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook*, Freeling and Walbot, Eds., Springer, New York (1994); *Corn and Corn Improvement*, 3rd edition, Sprague and Dudley Eds., American Society of Agronomy, Madison, Wis. (1988). For transformation and regeneration of maize see, Gordon-Kamm et al., *The Plant Cell* 2:603–618 (1990).

The regeneration of plants containing the polynucleotide of the present invention and introduced by *Agrobacterium* from leaf explants can be achieved as described by Horsch et al., *Science*, 227:1229–1231 (1985). In this procedure, transformants are grown in the presence of a selection agent and in a medium that induces the regeneration of shoots in the plant species being transformed as described by Fraley et al., *Proc. Natl. Acad. Sci. USA* 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self-crossed to produce a homozygous inbred plant. The inbred plant produces seed containing the newly introduced heterologous nucleic acid. These seeds can be grown to produce plants that would produce the selected phenotype. Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences. Transgenic plants expressing a polynucleotide of the present invention can be screened for transmission of the nucleic acid of the present invention by, for example, standard immunoblot and DNA detection techniques. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

Transgenic plants of the present invention can be homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

Modulating Polypeptide Levels and/or Composition

The present invention further provides a method for modulating (i.e., increasing or decreasing) the concentration or ratio of the polypeptides of the present invention in a plant or part thereof. Modulation can be effected by increasing or decreasing the concentration and/or the ratio of the polypeptides of the present invention in a plant. The method comprises introducing into a plant cell a recombinant expression cassette comprising a polynucleotide of the present invention as described above to obtain a transgenic plant cell, culturing the transgenic plant cell under transgenic plant cell growing conditions, and inducing or repressing expression of a polynucleotide of the present invention in the transgenic plant for a time sufficient to modulate concentration and/or the ratios of the polypeptides in the transgenic plant or plant part.

In some embodiments, the concentration and/or ratios of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or ratios of polypeptides of the present invention in the plant. Plant forming conditions are well known in the art and discussed briefly, supra.

In general, concentration or the ratios of the polypeptides is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In some embodiments, the polypeptides of the present invention are modulated in monocots, particularly maize.

Molecular Markers

The present invention provides a method of genotyping a plant comprising a polynucleotide of the present invention. Optionally, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance.

See, e.g., Clark, Ed., *Plant Molecular Biology: A Laboratory Manual*. Berlin, Springer-Verlag, 1997. Chapter 7. For molecular marker methods, see generally, "The DNA Revolution" in: Paterson, A. H., *Genome Mapping in Plants* (Austin, Tex., Academic Press/R. G. Landis Company, 1996) pp. 7–21.

The particular method of genotyping in the present invention may employ any number of molecular marker analytic techniques such as, but not limited to, restriction fragment length polymorphisms (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the present invention.

In the present invention, the nucleic acid probes employed for molecular marker mapping of plant nuclear genomes selectively hybridize, under selective hybridization conditions, to a gene encoding a polynucleotide of the present invention. In some embodiments, the probes are selected from polynucleotides of the present invention. Typically, these probes are cDNA probes or restriction-enzyme treated (e.g., Pst I) genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRV, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In some embodiments, the nucleic acid probe comprises a polynucleotide of the present invention.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, *Nucleic Acids Res.* 15:8125 (1987)) and the 7-methylguanosine cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)). Accordingly, the present invention provides 5' and/or 3' untranslated regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host such as to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12:387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. WO 97/20078. See also, Zhang, J.-H., et al. *Proc. Natl. Acad. Sci. USA* 94:45044509 (1997). Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be a decreased $K_m$ and/or increased $K_{cat}$ over the wild-type protein as provided herein. In other embodiments, a protein or polynucleotide generated from sequence shuffling will have a ligand binding affinity greater than the non-shuffled wild-type polynucleotide. The increase in such properties can be at least 1 10%, 120%, 130%, 140% or at least 150% of the wild-type value.

Generic and Consensus Sequences

Polynucleotides and polypeptides of the present invention further include those having: (a) a generic sequence of at least two homologous polynucleotides or polypeptides, respectively, of the present invention; and, (b) a consensus sequence of at least three homologous polynucleotides or polypeptides, respectively, of the present invention. The generic sequence of the present invention comprises each species of polypeptide or polynucleotide embraced by the generic polypeptide or polynucleotide sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phyla, or kingdoms. For example, a polynucleotide having a consensus sequence from a gene family of Zea mays can be used to generate antibody or nucleic acid probes or primers to other Gramineae species such as wheat, rice, or sorghum. Alternatively, a polynucleotide having a consensus sequence generated from orthologous genes can be used to identify or isolate orthologs of other taxa. Typically, a polynucleotide having a consensus sequence will be at least 9, 10, 15, 20, 25, 30, or 40 amino acids in length, or 20, 30, 40, 50, 100, or 150 nucleotides in length. As those of skill in the art are aware, a conservative amino acid substitution can be used for amino acids which differ amongst aligned sequence but are from the same conservative substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous, or paralogous sequences as provided herein. Optionally, similar sequences used in generating a consensus or generic sequence are identified using the BLAST algorithm's smallest sum probability (P(N)). Various suppliers of sequence-analysis software are listed in chapter 7 of *Current Protocols in Molecular Biology*, F. M. Ausubel et al., Eds., Current Protocols, a joint venture between Greene Publishing Associates, Inc. and John Wiley & Sons, Inc. (Supplement 30). A polynucleotide sequence is considered similar to a reference sequence if the smallest sum probability in a comparison of the test nucleic acid to the reference nucleic acid is less than about 0.1, more preferably less than about 0.01, or 0.001, and most preferably less than about 0.0001, or 0.00001. Similar polynucleotides can be aligned and a consensus or generic sequence generated using multiple sequence alignment software available from a number of commercial suppliers such as the Genetics Computer Group's PILEUP software (GCG® Accelrys, San Diego, Calif.), Vector NTI's (North Bethesda, Md.) ALIGNX, or Genecode's (Ann Arbor, Mich.) SEQUENCHER. Conveniently, default parameters of such software can be used to generate consensus or generic sequences.

Assays for Compounds that Modulate Enzymatic Activity or Expression

The present invention also provides means for identifying compounds that bind to (e.g., substrates), and/or increase or decrease (i.e., modulate) the enzymatic activity of, catalytically active polypeptides of the present invention. The method comprises contacting a polypeptide of the present invention with a compound whose ability to bind to or modulate enzyme activity is to be determined. The polypeptide employed will have at least 20%, preferably at least 30% or 40%, more preferably at least 50% or 60%, and most preferably at least 70% or 80% of the specific activity of the native, full-length polypeptide of the present invention (e.g., enzyme). Generally, the polypeptide will be present in a range sufficient to determine the effect of the compound, typically about 1 nM to 10 µM. Likewise, the compound will be present in a concentration of from about 1 nM to 10 µM. Those of skill will understand that such factors as enzyme concentration, ligand concentrations (i.e., substrates, products, inhibitors, activators), pH, ionic strength, and temperature will be controlled so as to obtain useful kinetic data and determine the presence of absence of a compound that binds or modulates polypeptide activity. Methods of measuring enzyme kinetics is well known in the art. See, e.g., Segel, *Biochemical Calculations*, $2^{nd}$ Ed., John Wiley and Sons, New York (1976).

Detection of Nucleic Acids

The present invention further provides methods for detecting a polynucleotide of the present invention in a nucleic acid sample suspected of containing a polynucleotide of the present invention, such as a plant cell lysate, particularly a lysate of maize. In some embodiments, a cognate gene of a polynucleotide of the present invention or portion thereof can be amplified prior to the step of contacting the nucleic acid sample with a polynucleotide of the present invention. The nucleic acid sample is contacted with the polynucleotide to form a hybridization complex. The polynucleotide hybridizes under stringent conditions to a gene encoding a polypeptide of the present invention. Formation of the hybridization complex is used to detect a gene encoding a polypeptide of the present invention in the nucleic acid sample. Those of skill will appreciate that an isolated nucleic acid comprising a polynucleotide of the present invention should lack cross-hybridizing sequences in common with non-target genes that would yield a false positive result. Detection of the hybridization complex can be achieved using any number of well known methods. For example, the nucleic acid sample, or a portion thereof, may be assayed by hybridization formats including but not limited to, solution phase, solid phase, mixed phase, or in situ hybridization assays.

Detectable labels suitable for use in the present invention include any composition detectable by spectroscopic, radioisotopic, photochemical, biochemical, immunochemical, electrical, optical or chemical means. Useful labels in the present invention include biotin for staining with labeled streptavidin conjugate, magnetic beads, fluorescent dyes, radiolabels, enzymes, and colorimetric labels. Other labels include ligands which bind to antibodies labeled with fluorophores, chemiluminescent agents, and enzymes. Labeling the nucleic acids of the present invention is readily achieved such as by the use of labeled PCR primers.

Although the present invention has been described in some detail by way of illustration and example for purposes of clarity of understanding, it will be obvious that certain changes and modifications may be practiced within the scope of the appended claims.

EXAMPLE 1

This example describes the construction of a cDNA library.

The RNA for SEQ ID NO: 4 was isolated from night harvested ear shoot tissue (including the husk) of maize line B73 collected at the V-12 stage. SEQ ID NO: 5 was amplified from cDNA made from the RNA of whole kernels of maize line B73 collected 7 days after pollination. Total RNA can be isolated from maize tissues with TRIZOL Reagent (Life Technology Inc. Gaithersburg, Md.) using a modification of the guanidine isothiocyanate/acid-phenol procedure described by Chomczynski and Sacchi (Chomczynski, P., and Sacchi, N. *Anal. Biochem.* 162, 156 (1987)). In brief, plant tissue samples are pulverized in liquid nitrogen before the addition of the TRIZOL Reagent, and then further homogenized with a mortar and pestle. Addition of chloroform followed by centrifugation is conducted for separation of an aqueous phase and an organic phase. The total RNA is recovered by precipitation with isopropyl alcohol from the aqueous phase.

The selection of poly(A)+RNA from total RNA can be performed using POLYATTRACT system (Promega Corporation. Madison, Wis.). Biotinylated oligo(dT) primers are used to hybridize to the 3' poly(A) tails on mRNA. The hybrids are captured using streptavidin coupled to paramagnetic particles and a magnetic separation stand. The mRNA is then washed at high stringency conditions and eluted by RNase-free deionized water.

cDNA synthesis and construction of unidirectional cDNA libraries can be accomplished using the SUPERSCRIPT Plasmid System (Life Technologies Inc. Gaithersburg, Md.). The first strand of cDNA is synthesized by priming an oligo(dT) primer containing a Not I site. The reaction is catalyzed by SUPERSCRIPT Reverse Transcriptase II at 45° C. The second strand of cDNA is labeled with alpha-$^{32}$P-dCTP and a portion of the reaction analyzed by agarose gel electrophoresis to determine cDNA sizes. cDNA molecules smaller than 500 base pairs and unligated adapters are removed by SEPHACRYL-S400 chromatography. The selected cDNA molecules are ligated into pSPORT1 vector (Life Technologies Inc. Gaithersburg, Md.) in between Not I and Sal I sites.

Alternatively, cDNA libraries can be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

EXAMPLE 2

This example describes cDNA sequencing and library subtraction.

Individual colonies can be picked and DNA prepared either by PCR with M13 forward primers and M13 reverse primers, or by plasmid isolation. cDNA clones can be sequenced using M13 reverse primers.

cDNA libraries are plated out on 22×22 cm$^2$ agar plate at density of about 3,000 colonies per plate. The plates are incubated in a 37° C. incubator for 12–24 hours. Colonies are picked into 384-well plates by a robot colony picker, Q-bot (GENETIX Limited). These plates are incubated overnight at 37° C. Once sufficient colonies are picked, they are pinned onto 22×22 cm$^2$ nylon membranes using Q-bot. Each membrane holds 9,216 or 36,864 colonies. These membranes are placed onto an agar plate with an appropriate antibiotic. The plates are incubated at 37° C. overnight.

After colonies are recovered on the second day, these filters are placed on filter paper prewetted with denaturing solution for four minutes, then incubated on top of a boiling water bath for an additional four minutes. The filters are then placed on filter paper prewetted with neutralizing solution for four minutes. After excess solution is removed by placing the filters on dry filter papers for one minute, the colony side of the filters is placed into Proteinase K solution, incubated at 37° C. for 40–50 minutes. The filters are placed on dry filter papers to dry overnight. DNA is then cross-linked to nylon membrane by UV light treatment.

Colony hybridization is conducted as described by Sambrook, J., Fritsch, E. F. and Maniatis, T., (in Molecular Cloning: A Laboratory Manual, 2$^{nd}$ Edition). The following probes can be used in colony hybridization:

1. First strand cDNA from the same tissue as the library was made from to remove the most redundant clones.

2. 48–192 most redundant cDNA clones from the same library based on previous sequencing data.

3. 192 most redundant cDNA clones in the entire maize sequence database.

4. A Sal-A20 oligo nucleotide: TCG ACC CAC GCG TCC GAA AAA AAA AAA AAA AAA AAA, listed in SEQ ID NO. 3, removes clones containing a poly A tail but no cDNA.

5. cDNA clones derived from rRNA.

The image of the autoradiography is scanned into computer and the signal intensity and cold colony addresses of each colony is analyzed. Re-arraying of cold-colonies from 384 well plates to 96 well plates is conducted using Q-bot.

EXAMPLE 3

This example describes the cloning of the maize Mre11 polynucleotide sequence exemplified in SEQ ID NO. 1.

A 2.3 kb maize EST clone (clone Id #CMTNJ56) was found in a cDNA library prepared from mRNA isolated from night harvested ear shoot tissue (including the husk) of maize line B73 collected at the V-12 stage. This clone had an open reading frame of about 1.5 kb (Example 5) that showed a deduced protein sequence having homology to known eukaryotic MRE11 sequences. However, this clone did not appear to have the start codon (ATG) for MRE11 cDNA. Therefore, the remaining 5' end sequences for this maize orthologue of MRE11 was cloned using a library screening approach.

The library screening approach involves designing a set of nested, complementary oligonucleotides to be used as downstream or reverse primers based on the known EST sequence. These primers are then used in conjunction with a pair of nested upstream primers designed and synthesized based on the vector sequence in which the EST's are cloned (pSPORT1, Life Technologies Inc. Gaithersburg, Md.). A large set of cDNA libraries cloned in the same vector can then be screened using PCR.

A total of 106 cDNA libraries prepared from mRNA harvested from various maize tissues at different developmental stages or following various environmental or physiological stimuli (e.g. herbicide treatment, hormonal treatment etc.) were used for the screen. For the primary screen the primer M13R (5'AGCGGATMCMTTTCACACAG-GAAACAGCTATGAC 3', listed in SEQ ID NO: 6) and sequence specific primer R1 (5'CTTATTTTTATCTGCC-MTG 3', listed in SEQ ID NO: 7) were used. Amplification (for a total of 30 cycles) was initiated by denaturation at 94° C. for 2 min, followed by annealing at 55° C. for 45 sec. and elongation at 72° C. for 1 min. All the amplification reactions were carried out using Taq polymerase (Boehringer Mannheim, Indianapolis, Ind.). Products of the amplification reactions were analyzed by agarose gel electrophoresis. Putative candidates showing prominent bands were selected, diluted 1:10 with ddH$_2$O and used as substrates for secondary amplification reactions with the nested set of forward (T7 promoter sequence, 5'TMTACGACTCACTAT-AGGGCGAAT 3', listed in SEQ ID NO: 8) and reverse primers (R2–5'GCGTGACGGCTTGTTCTCAT 3', listed in SEQ ID NO: 9). The amplification conditions were the same as the primary PCR except that the annealing temperature was 56° C. instead of 55° C. The amplified products were analyzed by agarose gel electrophoresis and potential candidates cloned in the TopoTA vectors (Invitrogen, Carlsbad, Calif.) and representative clones sequenced.

One such clone, CMTNJ56-83-1, (amplified from a cDNA library prepared from mRNA isolated from whole kernels of maize line B73 collected 7 days after pollination) contained an approximately 0.4 kb cDNA fragment that encodes an open reading frame (Example 6) with extensive sequence homology to the N-terminal region of mammalian MRE11b. Further characterization of this clone clearly indicated the presence of the start codon ATG in the 5' region and a clear overlap with CMTNJ56 sequence. Plasmid DNA from this clone was used to construct the full length cDNA for maize MRE11 homologue 1 as follows:

1. CMTNJ56-83-1 was linearized at the unique SnaB1 site (Example 6).
2. CMTNJ56 was digested with SnaB1 to release a 2.2 kb fragment by taking advantage of the single SnaB1 site in the CMTNJ56 cDNA sequence (Example 5) and the unique SnaB1 site in the cloning vector pSPORT1.
3. Linearized CMTNJ56-83-1 and the 2.2 kb fragment of CMTNJ56 were isolated by running on low-melting agarose gels, followed by purification by ethanol precipitation.
4. The purified 2.2 kb fragment was ligated into the linearized CMTNJ56-83-1 vector using T4 DNA ligase (Boehringer Mannheim, Indianapolis, Ind.).
5. Ligation reaction products were used to transform competent E. coli DH5a cells (Life Technologies, Gaithersburg, Md.) and transformants were screened using the restriction enzyme BamH1.
6. Three potential candidate clones (CMTNJ56-FL-4, 5, and 8) showing the expected restriction pattern of two fragments of approximately 4.0 and 2.8 kb, were further confirmed by sequencing the plasmid DNA. All the clones show same nucleotide sequence for a full-length cDNA encoding a maize homologue of MRE11 (SEQ ID NO: 1).

EXAMPLE 4

This example shows the amino acid sequence of the maize Mre11 orthologue (SEQ ID NO: 2). The aspartic acid (D) involved in the nuclease function is identified in bold. Three motifs conserved in many members of the phosphodiesterase/Mre11 gene family are highlighted.

```
  1 MVGFCSALDL QQRIGLANTL SSGSMSEPAQ PSGGEGDVNT LLILVATDCH
 51 LGYMEKDEIR RFDSFQAFEE ICALADKNKV DFIIIGGDLF HENKPSRSTL
101 VKTIEILRRY CLNDQPVKFQ VVSDQTVNFP NRFGKVNYED PNFNVGLPVF
151 TIHGNHDDPA GVDNLSAIDI LSACNLVNYF GKMDLGGSGV GQIAVYPVLV
201 KKGMTSVALY GLGNIRDERL NRMFQTPHSV QWMRPGTQDG ESASDWFNIL

251 VLHQNRIKTN PKSAINEHFL PGSSVATSLI DGEAKPKHVL LLEIKGNQYR
301 PTKIPLRSVR PFEYAEVVLK DEADVNSNDQ DSVLEHLDKI VRNLIEKSSQ
351 PTASRSEPKL PLVRIKVDYS GFSTINPQRF GQKYVGKVAN PQDILIFSKS
401 AKKRQTTGDH IDDSEKLRPE ELNQQTIEAL VAESNLKMEI LPVDDLDIAL
451 HDFVNKDDKM AFYSCLQRNL EETRNKLSSE ADKSKFEEED IIVKVGECMQ
501 ERVKERSLHS KDGTRLTTGS HNLVFNYLSL NIFSFCIFPG AGYWTASNSY
551 NL*
```

EXAMPLE 5

This example shows the nucleotide sequence obtained from the EST clone named CMTNJ56 (SEQ ID NO: 4) which was cloned into the pSPORT vector. The sequences of the R1 and R2 primers are shown in bold. The unique SnaB1 site used to clone the N-terminal region and 5' upstream sequence encoded by the 396 bp fragment (shown in Example 6) is highlighted.

```
   1   CCGACTGCCA TCTAGGCTAC ATGGAGAAAG ATGAGATACC TAGGTTTGAT
  51   TCCTTTCAAG CATTTGAGGA GATTTGCGCA TTGGCAGATA AAAATAAGGT  (R2)
 101   GGATTTTATA CTTCTCGGTG GTGATCTATT CCATGAGAAC AAGCCGTCAC  (R1)
 151   GCTCAACCCT GGTAAAAACG ATTGAGATTC TACGGCGCTA CTGCCTAAAT
 201   GATCAACCTG TGAAGTTCCA GGTTGTCAGT GATCAGACAG TTAACTTTCC
 251   AAACAGGTTT GGTAAGGTAA ATTATGAAGA CCCAAACTTT AACGTTGGTC
 301   TGCCTGTGTT CACCATTCAT GGAAATCATG ATGACCCTGC TGGAGTGGAT
 351   AATCTCTCTG CTATCGATAT TCTTTCGGCT TGCAATCTTG TAAATTATTT
 401   TGGAAAGATG GACCTTGGTG GCTCTGGCGT TGGTCAGATA GCAGTTTATC
 451   CTGTACTTGT AAAAAAGGGC ATGACTTCAG TTGCACTGTA TGGTCTTGGA
 501   AACATTAGAG ATGAACGACT AAATAGAATG TTTCAGACGC CTCATTCAGT
 551   ACAGTGGATG CGACCTGGAA CTCAAGATGG GGAGTCAGCG TCTGACTGGT
 601   TCAATATATT GGTACTTCAT CAGAATAGGA TAAAGACAAA CCCTAAAAGT
 651   GCCATCAATG AGCATTTCTT ACCAGGTTCA TCAGTCGCGA CGTCCCTGAT
 701   TGATGGTGAA GCAAAACCAA AGCATGTTCT TTTGTTAGAA ATCAAGGGAA
 751   ATCAGTACAG GCCAACCAAA ATACCTCTGA GATCTGTCAG ACCTTTTGAA
 801   TATGCTGAGG TTGTGTTGAA AGATGAAGCA GATGTTAACT CAAATGATCA
 851   GGACTCTGTG CTTGAACATT TGGATAAAAT TGTAAGAAAT CTGATTGAGA
 901   AGAGTAGCCA ACCAACTGCC AGCAGATCAG AGCCCAAACT TCGATTAGTT
 951   AGAATCAAGG TAGATTACTC TGGGTTTTCA ACAATAAACC CACAACGTTT
1001   TGGTCAGAAG TATGTTGGAA AGGTCGCAAA CCCTCAAGAT ATTCTCATTT
1051   TCTCAAAATC AGCAAAGAAG CGCCAGACTA CAGGAGATCA CATTGATGAT
1101   TCTGAGAAAC TTCGTCCTGA GGAACTAAAC CAACAAACAA TCGAAGCTCT
1151   GGTCGCAGAG AGTAACTTGA AAATGGACAT TCTTCCGGTT GATGATTTGG
1201   ACATTGCGTT GCATGATTTT GTGAACAAGG ATGACAAGAT GGCATTTTAT
1251   TCATGTTTGC AGAGAAACCT TGAAGAAACC AGGAATAAGT TGAGTTCTGA
1301   AGCAGATAAA TCCAAATTTG AGGAAGAAGA TATAATAGTC AAAGTTGGCG
1351   AGTGCATGCA GGAACGCGTT AAGGAAAGGT CTCTGCACTC TAAGGACGGC
1401   ACACGTTTGA CAACAGGCTC TCACAACTTG GTGTTTAATT ATCTGAGCCT
1451   TAATATCTTT TCTTTTTGTA TTTTTCCTGG GGCTGGATAC TGGACAGCTA
1501   GTAACTCTTA CAACCTTTAA CTAGGATACT GGAGGTAAAT CTTTTACAGC
1551   TCAAAGCAAC CAGAACTCCT TCAGTGATGA TGAAGACACC AGGGAGATGC
1601   TTCTTGGTGC AAGATCAACT GATGTTGGAC GAAAATCATC TGGATTTACT
1651   AGACCCTCCA AAGATACTGC TGATGTTGCT AAACGTGGTA CTTCCAAAAG
1701   AGGCAGGGGA AGAGGCACCA GTTCAATGAA GCAGACCACT CTTAGTTTCA
1751   GCCAGTCAAG GTCAGCTACC GTTATTCGTA GTGAGGATGT GGCTTCCTCT
1801   GAGGAGGAAG CAGATGCAAA TGAAGTTGTT GAAAATTCAG AAGAGGAGAG
1851   TGCGCAACAA GTTGGACGTA AAAGAGCAGC TCCTAGGGGT AGAGGTAGAG
1901   GTAGAGGCGG AGGTTCCACT GCAAAGAGGG GGCGAAAAAC AGATATTGCT
1951   TCCATGCAAA ATATGATGAG CAAAGATGAT GATGATTCAG AAGATGAACC
2001   GCCAAAGAAA ACTCCTCGGG TCACCAGGAA CTATGGCGCT GTCAGGAGGA
2051   GATGACCCTT TAAGGAGTTC TTGCTCATGA GAGTTATAGG CTAGGTGTTT
2101   TGTCTTGTAA AGTTGGAAGA GCCGACGTGT TTTTATCAAC CTTGACGTCG
2151   ACCAGTTTGC GTTGCCGTGA ACTGACTGTA CCTTGTACAC GCCCGAATGT
2201   AACGGATTTT TGGGATTTAT ACATCCTTGT AGCTGCTTAA ATTCCAGCGA
2251   TTGCTGTCAA ATGAACTTCG GGAAAAAAAA AAAAAAAAAA AAAAAAAAAA
2301   AAAAAAAA
```

EXAMPLE 6

This example shows the nucleotide sequence of the N-terminal region of the maize Mre11 orthologue (SEQ ID NO: 5) which was obtained by sequencing the CMTNJ56-83-1 clone. Nucleotides 1–152 constitute the 5' untranslated region which contains two successive stop codons (indicated in bold) preceding the open reading frame (shown in italics). The initiation codon is indicated by bold italics. The underlined sequence overlaps perfectly with the 5' sequence of clone CMTNJ56 forming a contig. The unique SnaB1 site used for cloning the full-length cDNA is highlighted.

A. Transformation by Particle Bombardment.

Transformation of a mre11 construct along with a marker-expression cassette (for example, UBI::moPAT-GFPm::pinII) into genotype Hi-II follows a well-established bombardment transformation protocol used for introducing DNA into the scutellum of immature maize embryos (Songstad, D. D. et al., *In Vitro Cell Dev. Biol. Plant* 32:179–183,1996). It is noted that any suitable method of transformation can be used, such as *Agrobacterium*-mediated transformation and many other methods. To prepare suitable target tissue for transformation, ears are surface sterilized in 50% Chlorox bleach plus 0.5% Micro detergent for 20 minutes, and rinsed

```
  1 TCGACCCACG CGTCCGGCCG GCCCTTCTCT TCCCTTGCTG CTGTGCGAAC

51 CCGAGCGCCC AAACCTGAAC TTAAGCTATT TGGGGCTACT TGTATTTGGA

101 AAAAATATAT CGGGTCCTTT ACTGGTCCGC CGGTGTTATT TTAACTTATG

151 AAATGGTTGG TTTTTGCAGT GCATTAGATT TACAGCAACG GATTGGTTTG

201 GCCAACACGT TGAGTTCAGG TTCAATGTCT GAACCAGCAC AACCTAGTGG

251 AGGGGAAGGT GATGTCAACA CGCTCCTAAT ACTTGTAGCA ACCGACTGCC

301 ATCTAGGCTA CATGGAGAAA GATGAGATAC GTAGGTTTGA TTCCTTTCAA

351 GCATTTGAGG AGATTTGCGC ATTGGCAGAT AAAAATAAGG TGGATT
```

EXAMPLE 7

This example describes identification of the gene from a computer homology search.

Gene identities can be determined by conducting BLAST (Basic Local Alignment Search Tool; Altschul, S. F., et al., (1990) *J. Mol. Biol.* 215:403–410) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences are analyzed for similarity to all publicly available DNA sequences contained in the "nr" database using the BLASTN algorithm. The DNA sequences are translated in all reading frames and compared for similarity to all publicly available protein sequences contained in the "nr" database using the BLASTX algorithm (Gish, W. and States, D. J. *Nature Genetics* 3:266–272 (1993)) provided by the NCBI. In some cases, the sequencing data from two or more clones containing overlapping segments of DNA are used to construct contiguous DNA sequences.

Sequence alignments and percent identity calculations can be performed using the Megalign program of the LASERGENE bioinformatics computing suite (DNASTAR Inc., Madison, Wis.). Multiple alignment of the sequences can be performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method are KTUPLE 1, GAP PENALTY=3, WINDOW=5 and DIAGONALS SAVED=5.

EXAMPLE 8

This example provides methods of plant transformation and regeneration using the polynucleotides of the present invention, as well as a method to determine their effect on transformation efficiency.

two times with sterile water. The immature embryos (approximately 1–1.5 mm in length) are excised and placed embryo axis side down (scutellum side up), 25 embryos per plate. These are cultured onto medium containing N6 salts, Erikkson's vitamins, 0.69 g/l proline, 2 mg/l 2,4-D and 3% sucrose. After 4–5 days of incubation in the dark at 28° C., embryos are removed from the first medium and cultured onto similar medium containing 12% sucrose. Embryos are allowed to acclimate to this medium for 3 h prior to transformation. The scutellar surface of the immature embryos is targeted using particle bombardment. Embryos are transformed using the PDS-1000 Helium Gun from Bio-Rad at one shot per sample using 650 PSI rupture disks. DNA delivered per shot averages approximately 0.1667 kg. Following bombardment, all embryos are maintained on standard maize culture medium (N6 salts, Erikkson's vitamins, 0.69 g/l proline, 2 mg/l 2,4-D, 3% sucrose) for 2–3 days and then transferred to N6-based medium containing 3 mg/L Bialaphos®. Plates are maintained at 28° C. in the dark and are observed for colony recovery with transfers to fresh medium every two to three weeks. After approximately 10 weeks of selection, selection-resistant GFP positive callus clones can be sampled for presence of mre11 mRNA and/or protein. Positive lines are transferred to 288J medium, an MS-based medium with lower sucrose and hormone levels, to initiate plant regeneration. Following somatic embryo maturation (2–4 weeks), well-developed somatic embryos are transferred to medium for germination and transferred to the lighted culture room. Approximately 7–10 days later, developing plantlets are transferred to medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to Classic™ 600 pots (1.6 gallon) and grown to maturity. Plants are monitored for expression of mre11 mRNA and/or protein. Recovered colonies and plants are scored based on GFP visual expression, leaf painting sensitivity to a 1% application of Ignite® herbicide, and molecular characterization via PCR and Southern analysis.

B. Transformation by *Agrobacterium*

Transformation of a mre11 cassette along with UBI::moPAT~moGFP::pinII into a maize genotype such as Hi-II (or inbreds such as Pioneer Hi-Bred International, Inc. proprietary inbreds N46 and P38) is also done using the *Agrobacterium* mediated DNA delivery method, as described by U.S. Pat. No. 5,981,840 with the following modifications. Again, it is noted that any suitable method of transformation can be used, such as particle-mediated transformation, as well as many other methods. *Agrobactetium* cultures are grown to log phase in liquid minimal-A medium containing 100 μM spectinomycin. Embryos are immersed in a log phase suspension of Agrobacteria adjusted to obtain an effective concentration of 5×108 cfu/ml. Embryos are infected for 5 minutes and then co-cultured on culture medium containing acetosyringone for 7 days at 20° C. in the dark. After 7 days, the embryos are transferred to standard culture medium (MS salts with N6 macronutrients, 1 mg/L 2,4-D, 1 mg/L Dicamba, 20 g/L sucrose, 0.6 g/L glucose, 1 mg/L silver nitrate, and 100 mg/L carbenicillin) with 3 mg/L Bialaphos® as the selective agent. Plates are maintained at 28° C. in the dark and are observed for colony recovery with transfers to fresh medium every two to three weeks. Positive lines are transferred to an MS-based medium with lower sucrose and hormone levels, to initiate plant regeneration. Following somatic embryo maturation (2–4 weeks), well-developed somatic embryos are transferred to medium for germination and transferred to the lighted culture room. Approximately 7–10 days later, developed plantlets are transferred to medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to Classic™ 600 pots (1.6 gallon) and grown to maturity. Recovered colonies and plants are scored based on GFP visual expression, leaf painting sensitivity to a 1% application of Ignite® herbicide, and molecular characterization via PCR and Southern analysis.

C. Determining Changes in Transformation Efficiency

It is expected that transformation frequency will be improved by introducing mre11 using *Agrobacterium* or particle bombardment. Plasmids described in this example are used to transform Hi-II immature embryos using particle delivery or the *Agrobacterium*. The effect of mre11 can be measured by comparing the transformation efficiency of mre11 constructs co-transformed with GFP constructs to the transformation efficiency of control GFP constructs only. Source embryos from individual ears will be split between the two test groups in order to minimize any effect on transformation efficiency due differences in starting material. Bialaphos resistant GFP+ colonies are counted using a GFP microscope and transformation frequencies are determined (percentage of initial target embryos from which at least one GFP-expressing, bialaphos-resistant multicellular transformed event grows). In both particle gun experiments and *Agrobacterium* experiments, transformation frequencies are expected to be greatly increased in the mre11 treatment group.

D. Transient Expression of the Mre11 Polynucleotide Product

It may be desirable to transiently express Mre11 in order to increase the transformation efficiency of another polynucleotide of interest without incorporating the mre11 polynucleotide into the genome of the target cell. This can be done by delivering mre11 5'capped polyadenylated RNA or expression cassettes containing mre11 DNA. These molecules can be delivered using a biolistics particle gun. For example 5' capped polyadenylated mre11 RNA can easily be made in vitro using Ambion's mMessage mMachine kit. Following the procedure outlined above, RNA is co-delivered along with DNA containing an agronomically useful expression cassette. The cells receiving the RNA will transiently express Mre11 which will facilitate the integration of the polynucleotide or modification of interest. Plants regenerated from these embryos can then be screened for the presence of the gene or modification of interest.

The above examples are provided to illustrate the invention but not to limit its scope. Other variants of the invention will be readily apparent to one of ordinary skill in the art and are encompassed by the appended claims. All publications, patents, patent applications, and computer programs cited herein are hereby incorporated by reference.

What is claimed is:

1. An isolated protein comprising the amino acid sequence encoded by SEQ ID NO: 1, wherein the protein has 3' to 5' exonuclease activity.

2. An isolated protein comprising the amino acid sequence of SEQ ID NO: 2.

* * * * *